US008137710B2

(12) United States Patent
An et al.

(10) Patent No.: US 8,137,710 B2
(45) Date of Patent: Mar. 20, 2012

(54) **TREATING IDIOPATHIC THROMBOCYTOPENIC PURPURA WITH COMPRISING EXTRACTS OF *ASTRAGALUS MEMBRANACEUS***

(75) Inventors: Jinhua An, Santa Clara, CA (US); John M. Fidler, Oakland, CA (US); John H. Musser, San Carlos, CA (US)

(73) Assignee: EcoPharm Corporation, Taipei (TW)

( * ) Notice: Subject to any disclaimer, the term of this patent is extended or adjusted under 35 U.S.C. 154(b) by 196 days.

(21) Appl. No.: 12/638,845

(22) Filed: Dec. 15, 2009

(65) Prior Publication Data

US 2010/0158861 A1 Jun. 24, 2010

Related U.S. Application Data

(60) Provisional application No. 61/122,586, filed on Dec. 15, 2008.

(51) Int. Cl.
*A01N 65/00* (2009.01)

(52) U.S. Cl. ..................................................... 424/725

(58) Field of Classification Search ........................ None
See application file for complete search history.

(56) References Cited

U.S. PATENT DOCUMENTS

| | | | |
|---|---|---|---|
| 4,708,949 A | 11/1987 | Liu | |
| 4,795,742 A | 1/1989 | Liu | |
| 4,843,067 A | 6/1989 | Liu | |
| 4,944,946 A | 7/1990 | Liu | |
| 4,950,751 A | 8/1990 | DeWitt | |
| 5,116,969 A | 5/1992 | Adams et al. | |
| 5,268,467 A | 12/1993 | Verbiscar | |
| 5,336,506 A | 8/1994 | Josephson et al. | |
| 5,478,576 A | 12/1995 | Jung et al. | |
| 5,554,386 A | 9/1996 | Groman et al. | |
| 5,589,591 A | 12/1996 | Lewis | |
| 5,646,029 A | 7/1997 | Chen et al. | |
| 5,679,323 A | 10/1997 | Menz et al. | |
| 5,756,098 A | 5/1998 | Price et al. | |
| 5,770,217 A | 6/1998 | Kutilek, III et al. | |
| 5,830,747 A | 11/1998 | Chen et al. | |
| 6,991,817 B2 | 1/2006 | An et al. | |

FOREIGN PATENT DOCUMENTS

| | | |
|---|---|---|
| CN | 1 047 296 | 11/1990 |
| CN | 1 047 806 | 12/1990 |
| EP | 0 441 278 | 8/1991 |
| EP | 0 511 932 | 11/1992 |
| EP | 0 668 072 | 8/1995 |
| KR | 10-0195884 | 6/1999 |
| KR | 10-2002-0089817 | 11/2002 |
| KR | 10-2003-0091921 | 12/2003 |
| KR | 10-0526404 | 11/2005 |
| KR | 10-0697212 | 3/2007 |
| KR | 10-0760384 | 9/2007 |
| WO | WO 01/00682 | 1/2001 |
| WO | WO 02/02607 | 1/2002 |

OTHER PUBLICATIONS

International Search Report for PCT/US2000/018180, Nov. 8, 2000, Pharmagenesis, Inc.
International Search Report for PCT/US2001/020828, Sep. 18, 2002, Pharmagenesis, Inc.
International Search Report for PCT/US2009/068062, Sep. 30, 2010, EcoPharm, LLC.
Bensky, D. et al., "Radix Astragali", Chinese Herbal Medicine, *Materia Medica*, Sixth Printing, 1991, 457-459.
Chang. H-M. et al., "Huang qi", *Pharmacology and Applications of Chinese Materia Medica*, 1987, vol. II, 1041-1046.
Chu, D-T. et al., Immunotherapy with Chinese Medicinal Herbs II. Reversal of Cyclophosphamide-Induced Immune Suppression by Administration of Fractionated *Astragalus membrane aceus* In Vivo, *J. Clin. Lab. Immunology*, 1988, 25(3): 125-129.
Chu, D-T. et al., Fractionated Extract of *Astragalus membranaceus*, A Chinese Medicial Herb, Potentiates LAK Cell Cytotoxicity, Generated by a Low Dose of Recombinant Interleukin-2, *J. Clin. Lab. Immunology*, 1988, 26(4): 183-187.
Chu, D., et al., Immunostimulant Containing Interleukin-2 and Substance $F_3$ from *Astragalus membranaceus* as Actty Enchancer, Chemical Abstracts Service, vol. 115:105995z, abstract, Nov. 28, 1990, Abstract of Chinese Patent No. 1047298.
Hsu, H-Y., "Astragali Radix", *Oriental Materia Medica a Concise Guide*, 1986, 521.
Larm, O. et al., Structured Studies on a Water-Soluble Arabinogalactan Isolated from Rapeseed ((*Brassica napus*), *Acta Chemica Scandinavica*, 1976, B 30: 627-630.
McLaughlin, M.A., identification of Immunostimulants Derived from the Plant *Astragalus membraneceaus*, *Dissertation Abstracts International*, Jan. 1987, 47(7): 2891.
Miura, S. et al., Effect of a Traditional Chinese Herbal Medicine Ren-Shen-Yang-Rong-Tang (Japanese Name: Ninjin-Youei-To) On Hematopoietic stem Cells in Mice, *Int. J. Immunopharmac.*, 1989, vol. 11(7): 771-780.
Nothnagel, E.A., Proteoglycans and Related Components in Plant Cells, *International Review of Cytology*, vol. 174, 195-289.
Ohnishi, Y. et al., Effects of Juzen-Taiho-Toh (TJ-48), a Traditional Oriental Medicine, on Hematopoietic Recovery from Radiation Injury in Mice, *International Society for Experimental Hematology*, 1990, 18-22.
Quan, H.X. et al., Experimental Studies on the Action of Antiradiation of Membranous Milkvetch (*Astragalus membranaceus*), *Chinese Traditional and Herbal Drugs*, 1993, 24(8), 423-425. No Translation Available.

(Continued)

*Primary Examiner* — Michael Meller
(74) *Attorney, Agent, or Firm* — Syndicated Law; Brian S. Boyer

(57) ABSTRACT

The teachings provided herein generally relate to the preparation and uses of compositions comprising extracts of *Astragalus membranaceus*. The extracts are prepared from *Astragalus membranaceus* and can comprise, for example, an acid-modified arabinogalactan protein composition having an arabinose:galactose ratio ranging from about 3.5:1 to about 5.0:1, from about 5% to about 10% rhamnose, from about 15% to about 20% galactose, and from about 10% to about 15% glucose. The compositions can be used in the treatment of idiopathic thrombocytopenic purpura and the formulation of medicaments for such treatments.

12 Claims, 4 Drawing Sheets

OTHER PUBLICATIONS

Quan, H.X. et al., Effects of Radix Astragali on Hematopoiesis in Irradiated Mice, *China Journal of Chinese Malaria Medica*. Dec. 1994, 19(12), 741-743.

Rou, M. et al., The effect of Radix Astragall on Mouse Marrow Hematopoiesis: *Journal of Traditional Chinese Medicine*, 1983, 3(3): 199-204.

Rui, J. at al., Effects of Shi-ka-ron and Chinese Herbs in Mice Treated with Anti-Tumor Agent Mitomycin C, *Chung-Kuo chung His i Chieh Ho Tsa Chih 15*, No. 2, 101.

Sommer-Knudsen, J. et al., Hydroxyproline-Rich Plant Glycoproteins, *Phytochemistry*, 1998, 47(4): 483-497.

Sun, Y. et al., Preliminary Observations on the Effects of the Chinese Medicinal Herbs *Astragaius membranaceus* and *Ligustrum lucidum* on Lymphocyte Blastogenic Responses, *Journal of Biological responses Modifiers*, 1983, vol. 2, 227-237.

Tang, W. et al., "*Astragalus membranecus* (Fisch.) Bge.", Chinese drugs of Plant Origin, 1992, 191-197.

Xiao-Sheng, W. et al., Treatment of Leucopenia with Pure Astragalus Preparation—An Analysis of 115 Leucopenic Cases, Zhongguo Zhongxiyi Jieho Zazhi, *Chinese J. Inter. Trad. Western Med.*, 1995, 15(8): 462-464. No Translation Available.

Zhao, K.S. et al., Enhancement of the Immune Response in Mice by *Astragalus membranaceus* Extracts, *Immunopharmacology*, 1990, 20(3): 225-234.

Zhao, K.W. et al., Effect of Astragalan on Secretion of Tumor Necrosis Factors in Human Peripheral Blood Mononuclear Cells, *Chung-Kuo Chung His i Chieh Ho Tsa Chih 13*, No. 5, 263-259.

Handbook of Instrumental Techniques for Analytical Chemistry, ed. Frank Settle, Chapter 46, 853-866 (Chapter Author: david Meunier), Published by Prentice-Hall, 1997 (ISBN No. 013177380).

TREATING IDIOPATHIC THROMBOCYTOPENIC PURPURA WITH COMPRISING EXTRACTS OF *ASTRAGALUS MEMBRANACEUS*

CROSS-REFERENCE TO RELATED APPLICATIONS

This application claims the benefit of U.S. Provisional Application No. 61/122,586, filed Dec. 15, 2008, which is hereby incorporated herein by reference in its entirety.

BACKGROUND

1. Field of the Invention

The teachings provided herein relate to the preparation and uses of compositions comprising extracts of *Astragalus membranaceus*.

2. Description of Related Art

A decrease in the number of platelets or megakaryocytes is a condition known as thrombocytopenia, a condition experienced in a number of diseases, as well as treatments that suppress bone marrow function, suppress hematopoiesis, or cause a reduction in platelet count or megakaryocytes. Cancer patients, for example, are often treated with chemotherapy or radiation therapy and experience thrombocytopenia, increasing their risk of bleeding and potentially limiting the dose of the chemotherapeutic agent. There are at least two mechanisms that create thrombocytopenia—(1) a mechanism that reduces the production of megakaryocytes or platelets; and (2) a mechanism that acts to breakdown or remove the platelets from the circulation.

An example of a disease that uses the second mechanism is idiopathic thrombocytopenic purpura (ITP). ITP is an autoimmune hematological disease that is characterized by an attack by the immune system that destroys platelets in the blood, resulting in an abnormally low platelet count. The platelet destruction is due to the presence of antiplatelet autoantibodies, which are antibodies directed against the patient's own platelets. This low platelet count can lead to easy bruising, bleeding gums and, less commonly, to severe internal bleeding. Bleeding from the nose, gums, gastrointestinal or urinary tracts may also occur, and bleeding within the brain is a rare but feared complication.

Currently, ITP affects approximately 200,000 people in the United States, and there is no known cure. About half of all cases are classified as "idiopathic," meaning the cause is unknown. The term "thrombocytopenic" refers to the decrease in platelets, and the term "purpura" refers to the purplish areas in the skin and mucous membranes, such as the mouth lining, where bleeding has occurred due to the decreased platelets. The term "immune thrombytopenic purpura" is often used to describe the condition, as it specifies the immune nature of the disease and includes cases having known causes as well as cases of unknown origin.

ITP can be triggered by drugs, or associated with infection, pregnancy, or immune disorders, such as systemic lupus erythematosus. Acute ITP most commonly occurs in young children. Boys and girls are equally affected, and symptoms often follow a viral infection. About 85% of children recover within 1 year, and the problem does not return. ITP is considered chronic when it lasts more than 6 months, and the onset of chronic ITP can occur at any age. ITP peaks in adulthood and females are affected two to three times more often than males. Unfortunately, lifestyle changes are often required to prevent bleeding due to injury.

In some embodiments, standard ITP treatments use high-dose corticosteroids. Patients respond to the high-dose corticosteroids, but the responses are not durable, and the treatments are poorly tolerated with significant side-effects. And, failure or intolerance to corticosteroids can lead to the choice of a splenectomy, as the spleen is the major site of platelet destruction which, of course, leads to additional complications. In some embodiments, treatments can include administration of prednisone and/or IV immune globulin. Other drugs such as vincristine, azathioprine (IMURAN), DANAZOL, cyclophosphamide, and cyclosporine can also be used.

One of skill in the art will appreciate that abnormally low platelet counts are known to result from treatment with chemotherapeutic drugs or radiation treatments. These treatments provide the first mechanism described above in that they suppress bone marrow function, reduce the production of megakaryocytes and, in turn, reduce the platelet count. In contrast, the abnormally low platelet counts of ITP result from the second mechanism that removes platelets from the circulation through the creating of antibodies that bind to the platelets. Accordingly, those of skill in the art will appreciate a composition that can treat thrombocytopenia regardless of whether its due to a damaged biological process of creating the megakaryocytes or platelets in the circulation, or due to the antibody-mediated mechanism of ITP.

SUMMARY

The teachings provided herein generally relate to the preparation and uses of compositions comprising extracts of *Astragalus membranaceus*. In some embodiments, a composition comprising a high-yield extract of *Astragalus membranaceus*, wherein the extract comprises an arabinose:galactose ratio greater than about 3.5:1; from about 5% to about 10% rhamnose; from about 15% to about 20% galactose; from about 10% to about 20% galacturonic acid; and, from about 10% to about 15% glucose. In these embodiments, the high-yield extract is prepared using a first process that includes isolating a crude extract from *Astragalus membranaceus* and mildly treating the crude extract with an acid, the mildly treating including applying the acid to the crude extract at a concentration ranging from about 0.05M to about 0.5M, at a temperature ranging from about 15° C. to 25° C., and for a time ranging from about 1 hour to about 24 hours. The temperature and time for applying the acid are selected to obtain the arabinose:galactose ratio, the galactose content, the glucose content, and a high yield. The high yield is substantially higher than a yield of an extract of the *Astragalus membranaceus* produced using a second process that includes applying the acid to the crude extract at a temperature and time selected to obtain an arabinose:galactose ratio of less than 3.5:1, 20%-35% galactose, and less than about 10% glucose. In some embodiments, the acid used in the acid treatment is trichloroacetic acid or hydrochloric acid.

In some embodiments, the extract is isolated from the roots of *Astragalus membranaceus*. In these embodiments, the *Astragalus membranaceus* can be *A. membranaceus* Bge. var. *mongholicus* (Bge.) Hsiao or *A. membranaceus* (Fisch.) Bge. In some embodiments, the *Astragalus membranaceus* was grown in Inner Mongolia or Shanxi province, Peoples' Republic of China. Moreover, in some embodiments, the roots can be from *Astragalus membranaceus* plants that are about two years of age.

The compositions of the extracts can vary, and in some embodiments, the extracts have a weight-average molecular weight of at least 100 kiloDaltons, have at least 80% by weight carbohydrate and not more than 2% by weight protein, have an arabinose:galactose ratio ranging from about 4.0:1 to about 4.5:1, have a pH in aqueous solution ranging from about 4.5 to about 6.5, or any combination thereof.

The compositions comprising the extract can further comprise an agent that stimulates hematopoiesis or be administered in combination with an agent that stimulates hematopoiesis. In some embodiments, the agent can be selected from the group consisting of granulocyte colony stimulating factor, granulocyte macrophage colony stimulating factor, erythropoietin and erythropoiesis stimulating protein, thrombopoietin, interleukin-3, and derivatives thereof. In some embodiments, the composition can be in an aqueous injectable formulation comprising a therapeutically effective amount of the composition and an aqueous injectable excipient.

In some embodiments, the extract comprises an arabinose: galactose ratio ranging from about 1.5:1 to about 3:1; from about 5% to about 15% arabinose; less than about 1.5% rhamnose; from about 3% to about 7% galactose; less than about 4% galacturonic acid; and, from about 70% to about 90% glucose. In these embodiments, the extract can have a weight-average molecular weight ranging from about 20 kiloDaltons to about 60 kiloDaltons, a pH in aqueous solution ranging from about 4.5 to about 6.5, or a combination thereof.

The teachings provided herein also include a method of stimulating the hematopoietic system of a mammal. The method comprises administering to the mammal an effective amount of the composition comprising the extracts taught herein. In some embodiments, the stimulating includes increasing platelet counts, increasing white blood cell counts, increasing lymphocyte counts, or a combination thereof.

In some embodiments, the methods further comprise the co-administration of a second active agent. In these embodiments, the second active agent can be a hematopoietic agent. The second active agent may be selected from the group consisting of granulocyte colony stimulating factor, granulocyte macrophage colony stimulating factor, erythropoietin and erythropoiesis stimulating protein, thrombopoietin, interleukin-3, and derivatives thereof.

The mammal can be any mammal in which the compositions are administered, whether for testing purposes or therapeutic purposes. In some embodiments, the mammal is a human and, in some embodiments, the human is suffering from bone marrow suppression. The bone marrow suppression can be the result of chemotherapy or radiation therapy.

The teachings also provide a method of preparing the extracts. The methods comprise isolating a crude extract from *Astragalus membranaceus* and mildly treating the crude extract with an acid. The mildly treating includes applying the acid to the crude extract at a concentration ranging from about 0.05M to about 0.5M, at a temperature ranging from about 15° C. to 25° C., and for a time ranging from about 1 hour to about 24 hours. The temperature and time for applying the acid are selected to obtain an arabinose:galactose ratio greater than about 3.5:1; from about 5% to about 10% rhamnose; from about 15% to about 20% galactose; from about 10% to about 20% galacturonic acid; from about 10% to about 15% glucose; and a high yield. The high yield is substantially higher than a yield of an extract of the *Astragalus membranaceus* produced using a second process that includes applying the acid to the crude extract at a temperature and time selected to obtain an arabinose:galactose ratio of less than 3.5:1, 20%-35% galactose, and less than about 10% glucose. In some embodiments, the arabinose:galactose ratio can reduced to within a range of about 4.0:1 to about 4.5:1, about 3.75:1 to about 4.5:1, about 3.8:1 to about 4.25:1, or any range therein.

The teachings also provide a method of treating idiopathic thrombocytopenic purpura, wherein the method comprises administering an effective amount of the extracts taught herein to a subject having idiopathic thrombocytopenic purpura. In some embodiments, the acid-modified arabinogalactan protein composition is administered in combination with a second active agent. In some embodiments, the second active agent can be selected from the group consisting of granulocyte colony stimulating factor, granulocyte macrophage colony stimulating factor, erythropoietin and erythropoiesis stimulating protein, thrombopoietin, interleukin-3, and derivatives thereof. And, in some embodiments, the compositions can be used in the manufacture of a medicament for treating idiopathic thrombocytopenic purpura in a mammal by administering the medicament in a therapeutically effective amount.

One of skill reading the teachings that follow will appreciate that the concepts can extend into additional embodiments that go well-beyond a literal reading of the claims, the inventions recited by the claims, and the terms recited in the claims.

DETAILED DESCRIPTION

Figure 1:
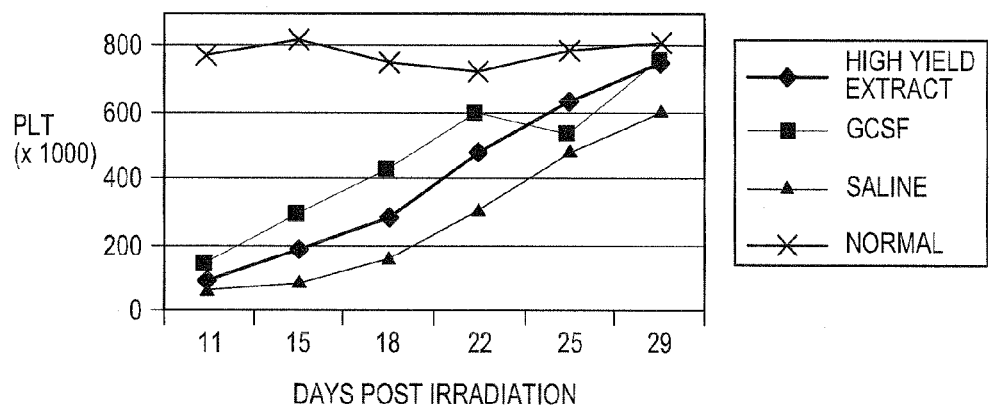
FIG. 1 shows the response of the platelet level in BALB/c mice to the high-yield extract following administration of a sublethal dose of radiation, according to some embodiments.

The teachings provided herein generally relate to the preparation and uses of compositions comprising extracts of *Astragalus membranaceus*. In some embodiments, the extracts can be used for stimulating hematopoiesis in myelosuppression; stimulating the production of IL-1$\beta$, IL-6, TNF-$\alpha$, IFN-$\gamma$, GM-CSF, or G-CSF; stimulating the production or action of white blood cells; stimulating the immune and/or hematopoietic system of a mammal having neutropenia, leukopenia, monocytopenia, anemia, or thrombocytopenia. The extracts can be used, for example, in treating conditions created by exposure to cytotoxic agents or radiation whether accidental or as part of a treatment program, where the conditions include, but are not limited to, hematopoietic cell damage, suppression, or removal, as a result of bone marrow suppression or immune response. Symptoms can be ameliorated using the treatments provided herein, where the symptoms can include, for example, cachexia, emesis, and drug withdrawal symptoms. Examples of such extracts can be found, for example, in U.S. Pat. No. 6,991,817 and WO200100682, each of which is hereby incorporated herein in entirety by reference.

The extracts stimulate hematopoietic activity and, thus, increase blood cell production. The extracts, for example, can increase platelet count and are effective at treating thrombocytopenia, a condition that is most commonly seen in patients undergoing cancer treatment. There are numerous other causes of thrombocytopenia, however, such as immune disorders and viral disorders. An example of an immune disorder is ITP, and an example of a viral disorder is HIV or chronic hepatitis. The administration of drugs can also cause thrombocytopenia, where a platelet count reduction can be seen as an adverse reaction to the drug, or a result of the drug suppressing bone marrow function. Anti-inflammatory medicines, cardiac medicines, antibiotics, have been identified as a cause of thrombocytopenia. Physical conditions, such as an enlarged spleen, can cause thrombocytopenia, as the enlarged spleen traps and destroys the platelets. Immune system illnesses, such as lupus and rheumatoid disease can also cause Thrombocytopenia.

As such, the extracts can be used in treating thrombocytopenia, for example, whether created by an immune disorder or a bone marrow suppression. The extracts can be used to stimulate production of white blood cells, as well. The compositions and methods described herein stimulate hematopoiesis, and induce the proliferation or maturation of megakaryocytes, and other white blood cells. The compositions and methods described herein stimulate the production, proliferation, and maturation of platelets, megakaryocytes, and other white blood cells, as well as accelerate their recovery after their production has been suppressed or they have been destroyed or removed from the circulation by a condition or other therapy. One of skill will better appreciate the scope of claims after reviewing the teachings that have been provided.

The extracts provided herein can assist in restoring the immune response to infection or in immunosuppressive conditions, and protecting hepatic cells in hepatitis B. And, the extracts could be reasonably expected to stimulate the growth and activity of primitive hematopoietic progenitors of the more mature hematopoietic cells. Moreover, the extracts can assist in improving the efficacy of an ongoing treatment program, such as chemotherapy, by strengthening a patient's resistance to infections by stimulating hematopoiesis in the patient and thwarting infections that would create a delay in administering treatments, or a reduction in intensity of treatments.

Preparation of an Extract of *Astragalus membranaceus* Having an Ara:Gal Ranging from about 1.5:1 to about 3:1 and an Average Molecular Weight Ranging from about 20K Daltons to about 60K Daltons ("the Purified Extract")

This teaching describes how an extract is isolated from *Astragalus membranaceus* and purified. In some embodiments, the roots of two-year old plants of *Astragalus membranaceus* provide a good source of the composition. In many embodiments, the roots can be from, for example, *A. membranaceus* Bge. var. *mongholicus* (Bge.) Hsiao; *A. membranaceus* (Fisch.) Bge.; or, *A. membranaceus* grown in Inner Mongolia or Shanxi province, Peoples' Republic of China.

The extract from the *Astragalus membranaceus* is typically derived from sterile processed chipped or sectioned dried roots. The preparation includes trimming the dried roots, scrubbing them with ultrafiltered (UF) water, and cleaning them with a disinfecting solution, such as 70% ethanol. The roots are cut into thin slices and dried under sterile conditions to produce "drink chips," also referred to herein as "clean chips." The extract is comprised of an arabinogalactan protein and associated polysaccharides that are isolated from the drink chips using a process that includes applying an aqueous extraction solvent having a temperature of at least 80-100° C.

The extraction solvent can be water and can optionally include a co-extractant, such as an alkali metal salt. The alkali metal salt can include, for example, potassium dihydrogen phosphate or sodium dihydrogen phosphate. The co-extractant can be, for example, at a concentration of 0.5M $KH_2PO_4$ at a pH of about 4.5).

The extraction solvent is applied to the drink chips for a time, temperature, and for as many extraction cycles needed to isolate the extract from the roots. A typical process includes three extraction cycles, each cycle lasting about 3 hours and applying an extraction solvent having a temperature of about 100° C. in some embodiments, the drink chips are extracted with an initial hot aqueous salt wash, such as in 0.5 M $KH_2PO_4$ at a pH of 4.5 and at a temperature of about 100° C. for about 30 minutes. In some embodiments, all steps following the preparation of the drink chips are conducted under aseptic conditions that include the use of sterile equipment and reagents.

The extraction solvent is then concentrated, and this can be done under vacuum at a temperature ranging from about 60° C. to about 70° C., to achieve a concentration of about 1 L per 1 kg of the drink chips. The concentration can also be accomplished using ultrafiltration, such as ultrafiltration with a 100 kiloDalton molecular weight cut-off filter.

The extract is then precipitated from the concentrated extraction solvent using a lower alkanol. The lower alkanol can be, for example, ethanol. In some embodiments, the ethanol can be added to the solvent to a concentration of about 70% ethanol at about room temperature to create the precipitate. In some embodiments, the precipitation is done by first using a lower concentration of about 35% ethanol in a first precipitation step, and then using a higher concentration of about 70% ethanol in a second precipitation step. The concentrations of lower alkanol used in the precipitations can range from, for example, 20%-30%, 30%-40%, 40%-50%, 50%-60%, 60%-70%, 70%-80%, 80%-90%, or any concentration therein.

The alkanol washes can be repeated for further purification. The precipitate, for example, can be washed with more of the lower alkanol, where a typical wash may include, for example, three washes with 95% ethanol. The precipitate is then suspended in water at a concentration suitable for further processing such as, for example, about 18-20% weight/volume. Reprecipitation by again adding a lower alkanol in the water can be used to remove additional materials that are not water-soluble. The supernatant can be precipitated with a higher concentration of the lower alkanol. The higher concentration of the lower alkanol can be, for example, 40-80% ethanol, and in some embodiments 60-70% ethanol, to create a crude extract precipitate that contains an arabinogalactan protein and associated polysaccharides.

The crude extract is re-dissolved in water and dried. Suitable drying processes can include any process known to one of skill that avoids excessive heating and can include, for example, spray drying, vacuum drying, freeze-drying, critical point drying, solvent exchange, and the like. The crude extract can also be re-dissolved in water or aqueous solution, wherein the crude extract is brought to a suitable concentration for ultrafiltration. In some embodiments, the suitable concentration for ultrafiltration is about 2%. The crude extract can then be ultrafiltered to further remove low molecular weight materials and reduce the volume of the solution, wherein the ultrafiltration system, for example, can have a 5 kiloDalton molecular weight cut-off.

In some embodiments, the crude extract can appear as a white to off-white powder, or light yellow powder, and is soluble in water to at least about 100 mg/mL. In some embodiments, the powder is soluble in water to at least about 200 mg/mL. The powder shows a weight loss upon drying of less than about 15%, has an endotoxin content of less than about 0.5 EU/mg and, in some embodiments, has an endotoxin content of less than about 0.3 EU/mg.

The crude extract can be further purified by ion-exchange chromatography. The composition is re-dissolved in an aqueous solution and brought to a suitable concentration for ultrafiltration, typically a concentration of about 2%. The redissolved composition is then ultrafiltered to further remove low molecular weight materials and reduce the volume of the solution. The 5 kiloDalton molecular weight cut-off ultrafiltration system described above can be used. The retentate of the ultrafiltration is eluted through a cation exchange column, such as a SP Sepharose cation exchange column equilibrated with 20 mM NaOAc buffer at pH 5.20. The eluate from the cation exchange column is eluted through an anion exchange column, such as a Q Sepharose anion exchange column equilibrated with the same NaOAc buffer.

The eluate from the anion exchange column may be (1) used directly in the preparation of other forms of the extract as taught herein; (2) concentrated and dried to form the crude extract, which can be kept as an intermediate suitable for preparation of the purified extract; or (3) used directly in the preparation of the purified extract.

In the preparation of the purified extract, the crude extract may be microfiltered through a suitable bacteriostatic filter, such as a 0.1 μm filter, and ultrafiltered to desalt the solution and again reduce its volume. An 8 kiloDalton molecular weight cut-off ultrafiltration may be used, in some embodiments. The retentate from the ultrafiltration is concentrated, and the percent concentration can be determined using a refractometer. In some embodiments, the retentate is concentrated to a concentration of about 20-26% at 50-60° C. The concentrated retentate is then precipitated with a lower alkanol. In some embodiments, the lower alkanol can be ethanol that is added to a concentration of about 80-90%. The precipitate may be further washed, where a typical wash can include three washes of the precipitate with anhydrous ethanol. The precipitate is then dried to give the purified extract. In some embodiments, the drying of the precipitate can occur, for example, through use of a vacuum oven at a temperature of about 60-70° C.

In order to decrease batch-to-batch variations in the extracts obtained from the process, the materials can be blended at one or more stages in the extraction process. In some embodiments, the process includes blending of the raw material, blending of the "drink chips", blending of other intermediates in the process, or a combination thereof.

The composition of the purified extract can be determined by gas-liquid chromatography of trimethylsilyl derivatives of a methanolyzed composition extract using standard analytical techniques known to one of skill. In some embodiments, the purified extract contains Ara in an amount ranging from about 5% to about 15%, about 5% to about 12%, about 5% to about 10%, about 10% to about 15%, or any range therein; Rha in an amount less than about 1% to 1.5%; GalA in an amount less than about 4%; Gal in an amount ranging from about 3% to about 7% Gal, about 3% to about 5%, about 4% to about 6%, or any range therein; Glc in an amount ranging from about 70% to about 90%, from about 70% to about 85%, from about 75% to about 80%, from about 85% to about 90%, or any range therein. All percents are expressed as mol %.

The Ara:Gal ratio in the purified extract ranges from about 1.5:1 to about 3:1. In some embodiments, the Ara:Gal ration ranges from about 1.5:1 to about 1.75:1, from about 1.75:1 to about 3:1, or any range therein.

The purified extract has a weight-average molecular weight ranging from about 20 kiloDaltons to about 60 kiloDaltons. In some embodiments, the molecular weight ranges from about 25 kiloDaltons to about 40 kiloDaltons, from about 27 kiloDaltons to about 35 kiloDaltons, or any range therein.

Moreover, the purified extract has an ash content of less than about 2% by weight, a heavy metal content of less than about 10 ppm by weight, and a hydroxyproline content of less than about 0.1%. In some embodiments, the hydroxyproline content is less than about 0.05%, less than about 0.03%, or any range therein.

The purified extract is substantially free of endotoxins, having an endotoxin content of less than 1.0 EU/mg, as determined by Endospecy [Seikagaku Corporation, Tokyo, Japan]. In some embodiments, the endotoxin content is less than 0.5 EU/mg, less than 0.3 EU/mg, or any range therein. And, the purified extract is soluble in water to at least 20 mg/ml and has a pH in aqueous solution ranging from about 4.5 to about 6.5.

In some embodiments, the extract comprises an arabinose:galactose ratio ranging from about 1.5:1 to about 3:1; from about 5% to about 15% arabinose; less than about 1.5% rhamnose; from about 3% to about 7% galactose; less than about 4% galacturonic acid; and, from about 70% to about 90% glucose. In these embodiments, the extract can have a weight-average molecular weight ranging from about 20 kiloDaltons to about 60 kiloDaltons, a pH in aqueous solution ranging from about 4.5 to about 6.5, or a combination thereof.

Preparation of an Extract of *Astragalus membranaceus* Having an Ara:Gal Ranging from about 2:1 to about 4:1 and an Average Molecular Weight that is Greater than about 100K Daltons ("the High Mw Extract")

Generally speaking the extracts of this example are higher molecular weight forms of the purified extracts, wherein the extracts have weight average molecular weights of at least 100 kiloDaltons. Among other advantages, these extracts have a lower volume. These higher molecular weight extracts are prepared using, generally, the procedures for preparing the purified extracts, wherein the eluate from the anion exchange column, the crude extract, or the purified extract may be used directly ("the purified extract or its intermediates").

A 100K molecular weight cut-off ultrafiltration system is used to prepare the high MW extract from the purified extract or its intermediates. For example, the eluate from the anion exchange column can be applied directly to the 100K molecular weight cut-off ultrafiltration system, and the retentate is concentrated, precipitated, optionally further washed, and dried, and each step can be accomplished using the methods described above in the preparation of the purified extract.

In some embodiments, the high MW extract contains Ara in an amount ranging from about 45% to about 75%, about 50% to about 75%, about 50% to about 65%, about 55% to about 60%, or any range therein; Rha in an amount ranging from about 2% to about 4%, about 2% to about 3%, or any range therein; GalA in an amount ranging from about 4% to about 6%, from about 4% to about 5%, or any range therein; Gal in an amount ranging from about 8% to about 25%, about 10% to about 20%, about 12% to about 18%, or any range therein; Glc in an amount ranging from about 5% to about 25%, from about 7% to about 20%, from about 10% to about 15%, or any range therein. All percents are expressed as mol %.

The Ara:Gal ratio in the high MW extract ranges from about 2:1 to about 4:1. In some embodiments, the Ara:Gal ration ranges from about 2:1 to about 3.75:1, about 2.5:1 to about 3.5:1, about 2.5:1 to about 3:1, about 3:1 to about 4:1, or any range therein.

The high MW extract has a weight-average molecular weight that is greater than 100 kiloDaltons. In some embodiments, the high MW extract has a weight-average molecular weight ranging from about 100 kiloDaltons to about 350 kiloDaltons. In some embodiments, the molecular weight ranges from about 100 kiloDaltons to about 300 kiloDaltons, about 125 kiloDaltons to about 275 kiloDaltons, about 150 kiloDaltons to about 250 kiloDaltons, about 200 kiloDaltons to about 275 kiloDaltons, or any range therein.

Moreover, the high MW extract has an ash content of less than about 2% by weight, a heavy metal content of less than about 20 ppm by weight, and a hydroxyproline content that is greater than about 0.2% and, in some embodiments, ranges from about 0.2% to about 0.3%.

The high MW extract is substantially free of endotoxins, having an endotoxin content of less than 1.0 EU/mg, as determined by Endospecy [Seikagaku Corporation, Tokyo, Japan]. In some embodiments, the endotoxin content is less than 0.5 EU/mg, less than 0.3 EU/mg, or any range therein. And, the purified extract is soluble in water to at least 10 mg/ml and has a pH in aqueous solution ranging from about 4.5 to about 6.5.

The high MW extract contains about 95% carbohydrates, including the carbohydrates that glycosylate the protein core of the arabinogalactan protein, and about 5% proteins, where hydroxyproline accounts for about 20% of the total amino acid content.

Preparation of an Extract of *Astragalus membranaceus* Having High Yield, an Ara:Gal Ranging from about 3.5:1 to about 5.0:1, and an Average Molecular Weight that is Greater than about 100K Daltons ("the High-Yield Extract")

An acid-modified extract is taught in U.S. Pat. No. 6,991, 817. Generally speaking, the extracts of this example are an improvement for at least the reason that they provide substantially higher yield forms of active extracts. In some embodiments, the high-yield extracts can be prepared using, generally, the procedures for preparing the high MW extract, and including the mild acid treatment described by this example.

The process includes isolating the crude extract and mildly treating the crude extract with an acid, the mildly treating including applying the acid to the crude extract at a concentration ranging from about 0.05M to about 0.5M, from about 0.01M to about 1.0M, from about 0.05M to about 0.1M, or any range therein. The process uses a treatment temperature ranging from about 15° C. to 25° C. and a treatment time ranging from about 1 hour to about 24 hours. Treatment can be increased beyond 24 hours, in some embodiments, to the length of time necessary for the action of a preferred hydrolysis technique. The temperature and time for applying the acid are selected to obtain the arabinose:galactose ratio of greater than 3.5:1, and other compositional features, such as the galactose content of about 15% to about 20%, the glucose content of about 10% to about 15%, and the high yield.

The yield is substantially higher than a yield of an extract of the *Astragalus membranaceus* produced using a different process that includes applying the acid to the crude extract at a temperature and time selected to obtain an arabinose:galactose ratio of less than 3.5:1, 20%-35% galactose, and less than about 10% glucose. The yield of the high-yield extract can be 3%-30% higher, 5%-25% higher, 10%-20% higher, 10%-15% higher, 15%-20% higher, 20%-30% higher, or any range therein. The high-yield extraction process produces arabinose:galactose ratios ranging from about 3.5:1 to about 5.0:1 and obtains such yields that are higher than the yield obtained using the other extract preparation process taught herein that produce extracts having an arabinose:galactose ratio of 3.5:1 or less.

The mild, acid treatment is selected to preserve polysaccharide chains, for example, while ensuring sufficient hydrolysis to achieve the desired purification and high yield. In some embodiments, the acid can comprise a mineral acid, an organic acid, or a combination thereof. In some embodiments, the organic acid is a weak organic acid. In some embodiments, the acid comprises trichloroacetic acid, hydrochloric acid, or a combination thereof. In some embodiments, the acid comprises formic acid, acetic acid, citric acid, or a combination thereof. In some embodiments, the acid comprises boric acid, phosphoric acid, hydrofluoric acid, or a combination thereof.

In some embodiments, the mild acid treatment can include hydrochloric acid in the range of about 0.01M to about 0.5M. In some embodiments, the hydrochloric acid can be substituted, or used in combination, with perchloric acid, hydroiodic acid, hydrobromic acid, sulfuric acid, nitric acid, or a combination thereof. In some embodiments, the acid can comprise an organic acid selected from the group consisting of dichloracetic acid, maleic acid, oxalic acid, salicyclic acid, trichloracetic acid, methansulfonic acid, trifluoroacetic acid, benzensulfonic acid, or a combination thereof. One of skill can readily select the appropriate concentrations and conditions.

In some embodiments, the acid concentration can be about 1.0M or lower, about 0.5M or lower, about 0.3M or lower, about 0.2M or lower, about 0.1M or lower, about 0.05M or lower, about 0.01M or lower, or any range therein. In some embodiments, the acid concentration can range from about 0.1M to about 0.5M, from about 0.2M to about 0.4M, from about 0.2M to about 0.3M, or any range therein. In some embodiments, the reaction time can range from 0.5 hrs to about 10 hrs, from about 1 hr to about 8 hrs, from about 2 hrs to about 7 hrs, from about 2 hrs to about 5 hrs, from about 2 hrs to about 3 hrs, or any range therein.

The high-yield extract can then be further purified using the ultrafiltration and ion-exchange procedures described above. The further purification removing more salts and low molecular weight materials, as well as reducing the volume of the solution.

In some embodiments, the high-yield extract contains Ara in an amount ranging from about 35% to about 65%, about 50% to about 65%, about 50% to about 60%, about 40% to about 60%, or any range therein; Rha in an amount ranging from about 5% to about 10%, about 5% to about 8%, about 6% to about 9%, or any range therein; GalA in an amount ranging from about 10% to about 20%, from about 10% to about 18%, about 12% to about 16%, or any range therein; Gal in an amount ranging from about 15% to about 25%, about 15% to about 20%, about 18% to about 21%, or any range therein; Glc in an amount of less than about 10%, from about 1% to about 8%, from about 2% to about 6%, or any range therein. All percents are expressed as mol %.

The Ara:Gal ratio in the high-yield extract is greater than about 3.5:1. In some embodiments, the Ara:Gal ratio ranges from about 3.5:1 to about 4.5:1, about 4.0:1 to about 4.5:1, about 3.5:1 to about 4:1, about 3.75:1 to about 4.5:1, or any range therein.

The high-yield extract has a weight-average molecular weight that is greater than 100 kiloDaltons. In some embodiments, the molecular weights range from about 100 kiloDaltons to about 350 kiloDaltons. In some embodiments, the molecular weight ranges from about 100 kiloDaltons to about 300 kiloDaltons, about 125 kiloDaltons to about 275 kiloDaltons, about 150 kiloDaltons to about 250 kiloDaltons, about 200 kiloDaltons to about 275 kiloDaltons, or any range therein.

Moreover, the high-yield extract has an ash content of less than about 2% by weight, a heavy metal content of less than about 20 ppm by weight, and a hydroxyproline content that is less than about 1.0%.

The high-yield extract is substantially free of endotoxins, having an endotoxin content of less than 1.0 EU/mg, as determined by Endospecy [Seikagaku Corporation, Tokyo, Japan]. In some embodiments, the endotoxin content is less than 0.5 EU/mg, less than 0.3 EU/mg, or any range therein. And, the purified extract is soluble in water to at least 10 mg/ml and has a pH in aqueous solution ranging from about 4.5 to about 6.5.

Glycans can comprise about 80% of an extract, with proteins, and possibly trace amounts of lipids, in the remainder. In some embodiments, the portion of the extract having a peak molecular weight of about 350 kiloDaltons, relative to pullulan sizing, represents the larger molecular weights, whereas the portion of the extract having a peak molecular weight of approximately of about 75 kiloDaltons represents the smaller molecular weights. The weight-average molecular weight of the portion having the larger molecular weights can be about 260 kiloDaltons and the portion having the smaller molecular weights can be about 120 kiloDaltons. The polydispersity can range, for example, from about 1 to about 5, from about 1.5 to about 3.5, or any range therein.

In some embodiments, the extract comprises an arabinose: galactose ratio greater than about 3.5:1; from about 5% to about 10% rhamnose; from about 15% to about 20% galactose; from about 10% to about 20% galacturonic acid; and, from about 10% to about 15% glucose.

One of skill will appreciate that the order of the steps provided above in the preparation of the extracts may be altered to achieve the same or similar result. In some embodiments, sequential ion-exchange chromatography steps can be used. In some embodiments, the ion-exchange chromatography can be done in a batch manner using the same or similar ion-exchange resins. The use of separate anion and cation resins can be replaced with the use of mixed-bed resins having both anion and cation exchange functions. In some embodiments, the ion-exchange purification can occur at various points in the process, including before or after the mild acid treatment, and the selection of molecular weight cut-off size in the ultrafiltration membranes can vary.

The compositions comprising any of the extract taught herein can further comprise an agent that stimulates hematopoiesis or be administered in combination with an agent that stimulates hematopoiesis. In some embodiments, the agent can be selected from the group consisting of granulocyte colony stimulating factor, granulocyte macrophage colony stimulating factor, erythropoietin and erythropoiesis stimulating protein, thrombopoietin, interleukin-3, and derivatives thereof. In some embodiments, the composition can be in an aqueous injectable formulation comprising a therapeutically effective amount of the composition and an aqueous injectable excipient.

Uses and Methods of Administration

The compositions can provide a therapeutic and/or prophylactic effect in the treatment of a disease, or ameliorization of one or more symptoms of a disease in a subject. The term "subject" and "patient" are used interchangeably and refer to an animal such as a mammal including, but not limited to, non-primates such as, for example, a cow, pig, horse, cat, dog, rat and mouse; and primates such as, for example, a monkey or a human.

The compositions provided herein can be administered for a variety of therapies described herein including, for example, the stimulation of hematopoiesis; inducing the proliferation or maturation of megakaryocytes; stimulating the production of IL-1-beta, IL-6, TNF-alpha., IFN-gamma, GM-CSF, or G-CSF; stimulating the production or action of white blood cells, neutrophils, treating neutropenia, leukopenia, monocytopenia, anemia, or thrombocytopenia. The compositions may also assist in accelerating recovery from exposure to cytotoxic agents or radiation, including accidental or non-therapeutic exposure, as well as therapeutic exposure.

The teachings provided herein also include a method of stimulating the hematopoietic system of a mammal. The method comprises administering to the mammal an effective amount of the composition comprising the extracts taught herein. In some embodiments, the stimulating includes increasing platelet counts, increasing white blood cell counts, increasing lymphocyte counts, or a combination thereof.

In some embodiments, the methods further comprise the co-administration of a second active agent. In these embodiments, the second active agent can be a hematopoietic agent. The second active agent may be selected from the group consisting of granulocyte colony stimulating factor, granulocyte macrophage colony stimulating factor, erythropoietin and erythropoiesis stimulating protein, thrombopoietin, interleukin-3, and derivatives thereof.

In many embodiments, the mammal can be any mammal in which the compositions are administered, whether for testing purposes or therapeutic purposes. In some embodiments, the mammal is a human and, in some embodiments, the human is suffering from bone marrow suppression. The bone marrow suppression can be the result of chemotherapy or radiation therapy.

The teachings also provide a method of treating idiopathic thrombocytopenic purpura, wherein the method comprises administering an effective amount of the extracts taught herein to a subject having idiopathic thrombocytopenic purpura. In some embodiments, the acid-modified arabinogalactan protein composition is administered in combination with a second active agent. In some embodiments, the second active agent can be selected from the group consisting of granulocyte colony stimulating factor, granulocyte macrophage colony stimulating factor, erythropoietin and erythropoiesis stimulating protein, thrombopoietin, interleukin-3, and derivatives thereof.

The teachings also include pharmaceutical compositions comprising the extracts in an amount that therapeutic and/or prophylactic in the prevention, treatment of a disease, and/or amelioration of symptoms of disease.

The amount of extract used in the compositions can vary according to factors such as type of disease, age, sex, and weight of the subject. Dosage regimens may be adjusted to optimize a therapeutic response. In some embodiments, a single bolus may be administered; several divided doses may be administered over time; the dose may be proportionally reduced or increased; or any combination thereof, as indicated by the exigencies of the therapeutic situation and factors known one of skill in the art. It is to be noted that dosage values may vary with the severity of the condition to be alleviated. Dosage regimens may be adjusted over time according to the individual need and the professional judgment of the person administering or supervising the administration of the compositions, and the dosage ranges set forth herein are exemplary only and do not limit the dosage ranges that may be selected by medical practitioners.

The terms "administration" or "administering" refer to a method of incorporating a composition into the cells or tissues of a subject, either in vivo or ex vivo to diagnose, prevent, treat, or ameliorate a symptom of a disease. In one example, a compound can be administered to a subject in vivo parenterally. In another example, a compound can be administered to a subject by combining the compound with cell tissue from the subject ex vivo for purposes that include, but are not limited to, assays for determining utility and efficacy of a composition. When the compound is incorporated in the subject in combination with one or active agents, the terms "administration" or "administering" can include sequential or concurrent incorporation of the compound with the other agents such as, for example, any agent described above. A pharmaceutical composition of the invention is formulated to be compatible with its intended route of administration. Examples of routes of administration include, but are not limited to, parenteral such as, for example, intravenous, intradermal, intramuscular, and subcutaneous injection; oral; inhalation; intranasal; transdermal; transmucosal; and rectal administration.

An "effective amount" of a compound of the invention can be used to describe a therapeutically effective amount or a prophylactically effective amount. An effective amount can also be an amount that ameliorates the symptoms of a disease. A "therapeutically effective amount" refers to an amount that is effective at the dosages and periods of time necessary to achieve a desired therapeutic result and may also refer to an amount of active compound, prodrug or pharmaceutical agent that elicits any biological or medicinal response in a tissue, system, or subject that is sought by a researcher, veterinarian, medical doctor or other clinician that may be part of a treatment plan leading to a desired effect. In some embodiments, the therapeutically effective amount may need to be administered in an amount sufficient to result in amelioration of one or more symptoms of a disorder, prevention of the advancement of a disorder, or regression of a disorder. In one example, treatment of an inflammatory disorder or an autoimmune disorder characterized by inflammation, a therapeutically effective amount preferably refers to the amount of a therapeutic agent that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the composition. The term "treating" refers to the administering one or more therapeutic or prophylactic agents taught herein.

A "prophylactically effective amount" refers to an amount that is effective at the dosages and periods of time necessary to achieve a desired prophylactic result such as, preventing or inhibiting the severity of a paletelet or white blood cell count drop, or reducing the nadir of the drop. Typically, a prophylactic dose is used in a subject prior to the onset of a disease, or at an early stage of the onset of a disease, to prevent or inhibit onset of the disease or symptoms of the disease. A prophylactically effective amount may be less than, greater than, or equal to a therapeutically effective amount.

In some embodiments, the administration can be oral. In other embodiments, the administration can be subcutaneous injection. In other embodiments, the administration can be intravenous injection using a sterile isotonic aqueous buffer. In another embodiment, the administration can include a solubilizing agent and a local anesthetic such as lignocaine to ease discomfort at the site of injection. In other embodiments, the administrations may be parenteral to obtain, for example, ease and uniformity of administration.

The compounds can be administered in dosage units. The term "dosage unit" refers to discrete, predetermined quantities of a compound that can be administered as unitary dosages to a subject. A predetermined quantity of active compound can be selected to produce a desired therapeutic effect and can be administered with a pharmaceutically acceptable carrier. The predetermined quantity in each unit dosage can depend on factors that include, but are not limited to, (a) the unique characteristics of the active compound and the particular therapeutic effect to be achieved, and (b) the limitations inherent in the art of creating and administering such dosage units.

A "pharmaceutically acceptable carrier" is a diluent, adjuvant, excipient, or vehicle with which the composition is administered. A carrier is pharmaceutically acceptable after approval by a state or federal regulatory agency or listing in the U.S. Pharmacopeial Convention or other generally recognized sources for use in subjects.

The pharmaceutical carriers include any and all physiologically compatible solvents, dispersion media, coatings, antibacterial and antifungal agents, isotonic and absorption delaying agents, and the like. Examples of pharmaceutical carriers include, but are not limited to, sterile liquids, such as water, oils and lipids such as, for example, phospholipids and glycolipids. These sterile liquids include, but are not limited to, those derived from petroleum, animal, vegetable or synthetic origin such as, for example, peanut oil, soybean oil, mineral oil, sesame oil, and the like. Water can be a preferred carrier for intravenous administration. Saline solutions, aqueous dextrose and glycerol solutions can also be liquid carriers, particularly for injectable solutions.

Suitable pharmaceutical excipients include, but are not limited to, starch, sugars, inert polymers, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain minor amounts of wetting agents, emulsifying agents, pH buffering agents, or a combination thereof. The compositions can take the form of solutions, suspensions, emulsion, tablets, pills, capsules, powders, sustained-release formulations and the like. Oral formulations can include standard carriers such as, for example, pharmaceutical grades mannitol, lactose, starch, magnesium stearate, sodium saccharine, cellulose, magnesium carbonate, and the like. See Martin, E. W. Remington's Pharmaceutical Sciences. Supplementary active compounds can also be incorporated into the compositions.

In some embodiments, the carrier is suitable for parenteral administration. In other embodiments, the carrier can be suitable for intravenous, intraperitoneal, intramuscular, sublingual or oral administration. In other embodiments, the pharmaceutically acceptable carrier may comprise pharmaceutically acceptable salts.

Pharmaceutical formulations for parenteral administration may include liposomes. Liposomes and emulsions are delivery vehicles or carriers that are especially useful for hydrophobic drugs. Depending on biological stability of the therapeutic reagent, additional strategies for protein stabilization may be employed. Furthermore, one may administer the drug in a targeted drug delivery system such as, for example, in a liposome coated with target-specific antibody. The liposomes will bind to the target protein and be taken up selectively by the cell expressing the target protein.

Therapeutic compositions typically must be sterile and stable under the conditions of manufacture and storage. The composition can be formulated as a solution, microemulsion, liposome, or other ordered structure suitable for a high drug concentration. In some embodiments, the carrier can be a solvent or dispersion medium including, but not limited to, water; ethanol; a polyol such as for example, glycerol, propylene glycol, liquid polyethylene glycol, and the like; and, combinations thereof. The proper fluidity can be maintained in a variety of ways such as, for example, using a coating such as lecithin, maintaining a required particle size in dispersions, and using surfactants.

In some embodiments, isotonic agents can be used such as, for example, sugars; polyalcohols that include, but are not limited to, mannitol, sorbitol, glycerol, and combinations thereof; and sodium chloride. Sustained absorption characteristics can be introduced into the compositions by including agents that delay absorption such as, for example, monostearate salts, gelatin, and slow release polymers. Carriers can be used to protect active compounds against rapid release, and such carriers include, but are not limited to, controlled release formulations in implants and microencapsulated delivery systems. Biodegradable and biocompatible polymers can be used such as, for example, ethylene vinyl acetate, polyanhydrides, polyglycolic acid, collagen, polyorthoesters, polylactic acid, polycaprolactone, polyglycolic copolymer (PLG), and the like. Such formulations can generally be prepared using methods known to one of skill in the art.

The compounds may be administered as suspensions such as, for example, oily suspensions for injection. Lipophilic solvents or vehicles include, but are not limited to, fatty oils such as, for example, sesame oil; synthetic fatty acid esters, such as ethyl oleate or triglycerides; and liposomes. Suspensions that can be used for injection may also contain substances that increase the viscosity of the suspension such as, for example, sodium carboxymethyl cellulose, sorbitol, or dextran. Optionally, a suspension may contain stabilizers or agents that increase the solubility of the compounds and allow for preparation of highly concentrated solutions.

In one embodiment, a sterile and injectable solution can be prepared by incorporating an effective amount of an active compound in a solvent with any one or any combination of desired additional ingredients described above, filtering, and then sterilizing the solution. In another embodiment, dispersions can be prepared by incorporating an active compound into a sterile vehicle containing a dispersion medium and any one or any combination of desired additional ingredients described above. Sterile powders can be prepared for use in sterile and injectable solutions by vacuum drying, freeze-drying, or a combination thereof, to yield a powder that can be comprised of the active ingredient and any desired additional ingredients. Moreover, the additional ingredients can be from a separately prepared sterile and filtered solution. In another embodiment, the extract may be prepared in combination with one or more additional compounds that enhance the solubility of the extract.

In some embodiments, the compounds can be administered by inhalation through an aerosol spray or a nebulizer that may include a suitable propellant such as, for example, dichlorodifluoromethane, trichlorofluoromethane, dichlorotetrafluoroethane, carbon dioxide, or a combination thereof. In one example, a dosage unit for a pressurized aerosol may be delivered through a metering valve. In another embodiment, capsules and cartridges of gelatin, for example, may be used in an inhaler and can be formulated to contain a powderized mix of the compound with a suitable powder base such as, for example, starch or lactose.

In some embodiments, a therapeutically or prophylactically effective amount of a composition may range in concentration from about 0.001 nM to about 0.10 M; from about 0.001 nM to about 0.5 M; from about 0.01 nM to about 150 µM; from about 0.01 nM to about 500 µM; from about 0.01 nM to about 1000 µM, or any range therein. In some embodiments, the compositions may be administered in an amount ranging from about 0.001 mg/kg to about 500 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.15 mg/kg to about 50 mg/kg, from about 0.5 mg/kg to about 10 mg/kg, or any range therein, wherein a human subject is assumed to average about 70 kg.

The present invention encompasses sustained release formulations for the administration of one or more agents. In some embodiments, the sustained release formulations can reduce the dosage and/or frequency of the administrations of such agents to a subject.

In some embodiments, an effective amount of an extract of this invention can range, for example, from about 10 mg/day to about and 1000 mg/day, from about 50 mg/day to about 500 mg/day, from about 100 mg/day to about 250 mg/day, or any range therein, for a human of average body mass. For treating cachexia, emesis, or drug withdrawal symptoms, or modifying biological responses or protecting hepatic cells in hepatitis B, a similar amount will be therapeutically effective. A person of ordinary skill in the art will be able without undue experimentation, having regard to that skill and this disclosure, to determine a therapeutically effective amount of the compositions of this invention for a given disease.

The compositions can be administered as a pharmaceutical formulation by injection. In some embodiments, the formulation can comprise the extract in combination with an aqueous injectable excipient. Examples of suitable aqueous injectable excipients are well known to persons of ordinary skill in the art, and they, and the methods of formulating the formulations, may be found in such standard references as Alfonso A R: Remington's Pharmaceutical Sciences, 17th ed., Mack Publishing Company, Easton Pa., 1985. Suitable aqueous injectable excipients include water, aqueous saline solution, aqueous dextrose solution, and the like, optionally containing dissolution enhancers for the acid-modified arabinogalactan protein composition, such as 3 10% mannitol or other sugars, 3 10% glycine or other amino acids.

Typically, when administered as a hematopoietic agent, the extract can be administered by subcutaneously, intramuscularly, intraperitoneally, or intravenously, injecting. In some embodiments, intravenous administration is used, and it can be continuous intravenous infusion over a period of a few minutes to an hour or more, such as around fifteen minutes. The amount administered may vary widely depending on the type of formulation, size of a unit dosage, kind of excipients, and other factors well known to those of ordinary skill in the art. The formulation may comprise, for example, from about 0.001% to about 10% (w/w), from about 0.01% to about 1%, from about 0.1% to about 0.8%, or any range therein, with the remainder comprising the excipient or excipients.

In some embodiments, the extract can be administered in conjunction with at least one other therapeutic agent for the disease state being treated, especially another agent capable of stimulating hematopoiesis such as, for example, erythropoietin, thrombopoietin, granulocyte colony stimulating factor (G-CSF), IL-3, and the like. In some embodiments, a therapeutically or prophylactically effective amount of an extract may be administered in an amount ranging from about 0.001 mg/kg to about 500 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.25 mg/kg to about 75 mg/kg, from about 0.5 mg/kg to about 50 mg/kg or any range therein, wherein a human subject is assumed to average about 70 kg.

The extracts can be administered in a combination with each other or with other agents. In some embodiments, the agents can be administered at points in time that vary by about 15 minutes, 30 minutes, 1 hour, 2 hours, 4 hours, 8 hours, 12 hours, 18 hours, 24 hours, 48 hours or 1 week in time. In some embodiments, at least one of the agents is an agent that stimulates the hematopoietic system. In other embodiments, the agents can include antiproliferatives, antineoplastics, antimitotics, anti-inflammatories, antiplatelets, anticoagulants, antifibrins, antithrombins, antibiotics, antiallergics, antioxidants, and any prodrugs, codrugs, metabolites, analogs, homologues, congeners, derivatives, salts and combinations thereof.

The extracts taught herein can be administered, for example, in combination with a hematopoietic agent that is administered in a therapeutically effective amount. A hematopoietic agent is a molecule that stimulates hematopoiesis. Examples of hematopoietic agents include, but are not limited to granulocyte colony stimulating factor (G-CSF), granulocyte macrophage colony stimulating factor (GM-CSF), erythropoietin and erythropoiesis stimulating protein, thrombopoietin, interleukin-3, and derivatives thereof. Examples of G-CSF include, but are not limited to, filgrastim (NEUPOGEN), and derivatives thereof, such as PEG-FILGRASTIM. An example of GM-CSF includes sagramostim (LEUKINE). An example of erythropoietin is epoetin alfa (EPREX). An example of erythropoiesis stimulating protein is darbepoetin alfa (NESP, ARANESP).

The hematopoietic agent can be administered in combination with the extracts taught herein, and can be administered, for example, for 30 minutes, 1 hour, 2 hours, 4 hours, 8 hours, 12 hours, 18 hours, 1 day, 2 days, 3 days, 4 days, 5 days, 6 days, 7 days, 8 days, 9 days, 10 days, 2 weeks, 3 weeks, 4 weeks, 6 weeks, 3 months, 6 months 1 year, any combination thereof, or any amount of time considered necessary by one of skill. The agents can be administered concomitantly, sequentially, or cyclically to a subject. Cycling therapy involves the administering a first agent for a predetermined period of time, administering a second agent for a second predetermined period of time, and repeating this cycling for any desired purpose such as, for example, to enhance the efficacy of the treatment. The agents can also be administered concurrently. The term "concurrently" is not limited to the administration of agents at exactly the same time, but rather means that the agents can be administered in a sequence and time interval such that the agents can work together to provide additional benefit. Each agent can be administered separately or together in any appropriate form using any appropriate means of administering the agent or agents.

In some embodiments, G-CSF is administered in combination with an extract taught herein using any amount, time, and method of administration known to be effective by one of skill. The G-CSF can be NEUPOGEN, for example, administered in an amount ranging from about 0.1 μg/kg to about 1 mg/kg, from about 0.5 μg/kg to about 500 μg/kg, from about 1 μg/kg to about 250 μg/kg, from about 1 μg/kg to about 100 μg/kg from about 1 μg/kg to about 50 μg/kg, or any range therein.

Articles of Manufacture

The present invention provides for articles of manufacture that encompass finished, packaged and labelled pharmaceutical products. The articles of manufacture include the appropriate unit dosage form in an appropriate vessel or container such as, for example, a glass vial or other container that is hermetically sealed. In the case of dosage forms suitable for parenteral administration, the active ingredient, e.g. one or more agents including an extract taught herein, is sterile and suitable for administration as a particulate-free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In some embodiments, the unit dosage form is suitable for intravenous, intramuscular, topical or subcutaneous delivery. Thus, the invention encompasses solutions, which are preferably sterile and suitable for each route of delivery. The concentration of agents and amounts delivered are included as described herein.

As with any pharmaceutical product, the packaging material and container are designed to protect the stability of the product during storage and shipment. In addition, the articles of manufacture can include instructions for use or other information material that can advise the user such as, for example, a physician, technician or patient, regarding how to properly administer the composition as a prophylactic, therapeutic, or ameliorative treatment of the disease of concern. In some embodiments, instructions can indicate or suggest a dosing regimen that includes, but is not limited to, actual doses and monitoring procedures.

In other embodiments, the instructions can include informational material indicating that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. The informational material should indicate that anaphylaxis can be fatal and may occur when any foreign protein is introduced into the body. The informational material should indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

In some embodiments, the articles of manufacture can comprise one or more packaging materials such as, for example, a box, bottle, tube, vial, container, sprayer, insufflator, intravenous (I.V.) bag, envelope, and the like; and at least one unit dosage form of an agent comprising an extract taught herein within the packaging material. In other embodiments, the articles of manufacture may also include instructions for using the composition as a prophylactic, therapeutic, or ameliorative treatment for the disease of concern.

In other embodiments, the articles of manufacture can comprise one or more packaging materials such as, for example, a box, bottle, tube, vial, container, sprayer, insufflator, intravenous (I.V.) bag, envelope, and the like; and a first composition comprising at least one unit dosage form of an agent comprising an extract as taught herein within the packaging material, along with a second composition comprising a second agent such as, for example, a glycosaminoglycan, phospholipid, poly(alkylene glycol), any other bioactive agent taught herein, or any prodrugs, codrugs, metabolites, analogs, homologues, congeners, derivatives, salts and combinations thereof. In other embodiments, the articles of manufacture may also include instructions for using the composition as a diagnostic, prophylactic, therapeutic, or ameliorative treatment for the disease of concern.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims.

EXAMPLE 1

Preparation of an Extract of *Astragalus membranaceus* Having an Ara:Gal Ranging from about 1.5:1 to about 3:1 and an Average Molecular Weight Ranging from about 20K Daltons to about 60K Daltons ("the Purified Extract" or EP011)

The purified extract has a 20-60 kilodalton MW and a 70-90% glucose composition.

The purified extract was prepared from chips of *Astragalus membranaceus* roots obtained from Inner Mongolia. The dried roots (300 kg) were processed into chips by cleaning with de-ionized water, then with ultrafiltered water. Portions of contaminated surface were removed and the roots were cut into chips with a thickness of 2-5 mm. The chips were then sterilized and dried.

The chips (200 kg) were extracted 3 times in a 3-ton aqueous extractor at 100° C. for 3 hours. The resulting aqueous extracts were combined and then concentrated 30-40 fold at 60-70° C. under reduced pressure. The resulting water extract was precipitated twice with 70% ethanol and one time with 35% ethanol. The ethanol precipitate was dissolved in water and spray-dried to generate a polysaccharide intermediate.

The polysaccharide intermediate (3.0 kg) was dissolved in water, microfiltered, ultrafiltered, and then sequentially purified first by a cation exchange column, then by an anion exchange column. The desired eluent was microfiltered and ultrafiltered before final concentration. The concentrate was finally lyophilized in bulk to produce the purified extract after blending.

The purified extract consists of polysaccharides of glucans, rhamnogalacturonans (RGs), arabinogalactans (AGs) and glycoprotein of arabinoglactan proteins (AGPs) with a weight average molecular weight of 20,000-60,000 daltons. The drug substance is a scentless, near white amorphous powder. It is readily soluble in water and saline with a pH of 4.5-6.5, slightly soluble in ethanol at low concentration, and insoluble in organic solvents like acetone.

The structures of polysaccharides and glycoproteins present in the purified extract were characterized and elucidated by a combination of glycosyl-residue compositions by TMS-GLC, glycosyl-linkage compositions by methylation of GLC-MS, $^1$H-NMR spectroscopy, amino acid compositions by AA analyzer, and MW distribution by size exclusion HPLC. The dominant glycosyl residues, determined by sugar composition analysis, are glucosyl (60-85 mole %), arabinosyl (5-20 mole %), and glactosyl (5-15 mole %) residues. Small amounts (2-5 mole %) of glacturonic acid and rhamnose are also present in this product. Glycosyl-linkage analysis shows that major glycosyl linkages for glucosyl residues are terminal, 4-, 6-, and 4,6-linked; arabinosyl residues are terminal, 5-, 3-, and 3,5-linked; galactosyl residues are terminal, 3-, 6-, and 3,6-linked; glacturonic acid is 4-linked; and rhamnosyl residues are 2-linked. Amino acid composition analysis showed that the glycoproteins present in this product are rich in Hyp, Asp, Thr, Ser, Glu, Pro, Gly, Ala, Val, and Lys residues.

Analysis of the Purified Extract

The glycosyl-residue composition analysis is shown in Table 1. The polysaccharides in the purified extract contain mainly glucosyl, arabinosyl, and galactosyl residues. Only small amount of rhamnose and galacturonic acid are present in the purified extract. Glycosyl-residue compositions of the purified extract were determined by analysis of per-0-trimethylsilylated methyl glycosides by GLC. The derivatives were separated in a J&W Scientific DB-1 column (0.25 mm×30 m) using an HP-5890 gas chromatograph.

TABLE 1

Glycosyl-residue compositions in the purified extract.

| Glycosyl-residue | Ara | Rha | GalA | Gal | Glc |
|---|---|---|---|---|---|
| Mole % in the purified extract | 8.1 | 0.6 | 2.0 | 5.4 | 83.9 |

Based on the glycosyl-linkage composition provided in Table 2, and 1H-nmr spectrometry analyses, the dominant polysaccharide in this product is a 1,4-linked glucan with a certain degree of branching at the 6 position of the backbone residues. Other polysaccharides present in the purified extract are arabinogalactans and rhamnogalacturonans which are cross-linked with each other. Glycosyl-linkages were determined by methylation analysis. The samples in Me$_2$SO were methylated by butyllithium and iodomethane. The methylated samples were purified using a SepPak C18 cartridge, and the carboxymethyl groups of the uronosyl residues reduced with lithium triethylborodeuteride. Partial methylated aldotols were then prepared and analysed by HP 5971 MSD-5890 GLC (combined GLC-MS).

TABLE 2

Glycosyl-linkage compositions in the purified extract.

| Glycosyl-linkage | Mole % |
|---|---|
| Terminal Araf | 6.2 |
| 5-linked araf | 2.8 |
| 3-linked araf | 0.3 |
| 3,5-linked araf | 0.5 |
| 2-linked rha | 0.6 |
| Terminal glcp | 12.0 |
| 4-linked glcp | 68.2 |
| 6-linked glcp | 0.9 |
| 4,6-linked glcp | 4.5 |
| Terminal galp | 1.5 |
| 3-linked galp | 0.4 |
| 6-linked galp | 0.6 |
| 3,6-linked galp | 0.3 |
| 4-linked galA | 0.9 |

The amino acid composition analysis shown in Table 3 below indicates that Hyp, Asp, Thr, Ser, Glu, Gly, Ala, and Lys are the major amino acid residues of the proteins in the purified extract. The amino acid compositions of the purified extract were analyzed by an Beckman 6300 amino acid analyzer using the Collagen hydrolysate analysis method. The sample was hydrolyzed by 6 N HCL at 110° C. for 24 hours, diluted and then injected into the HPLC system.

TABLE 3

Amino acid compositions in the purified extract.

| Amino Acid residue | Mole % |
|---|---|
| Hyp | 9.7 |
| Asp | 14.4 |
| Thr | 8.9 |
| Ser | 8.9 |
| Glu | 11.0 |
| Pro | 4.2 |
| Gly | 9.7 |
| Ala | 9.0 |
| Cys | 0.3 |
| Val | 4.5 |
| Met | 0.4 |
| Ile | 2.1 |
| Leu | 3.1 |
| Tyr | 1.0 |
| Phe | 1.0 |
| His | 2.1 |
| Lys | 8.1 |
| Arg | 2.0 |

Endotoxin removal is critical to production of the purified extract since the route of administration for the product is by injection. Some of the polysaccharides in this product are structurally related to endotoxin LPS. It is thus important to keep endotoxin out of the process from the start rather than remove it during manufacturing.

EXAMPLE 2

Preparation of an Extract of *Astragalus membranaceus* Having High Yield, an Ara:Gal Ranging from about 3.5:1 to about 5.0:1, and an Average Molecular Weight that is Greater than about 100K Daltons ("the High-Yield Extract" or EP011AM)

Use of milder acid conditions results in Ara:Gal ratios of >3.5 and an extract of a much higher yield than the purified extract or the high molecular weight extracts taught herein. In some embodiments, the Ara:Gal ratio is kept under 5.0 at the high yield.

The high-yield extract was prepared from chips of *Astragalus membranaceus* roots obtained from Inner Mongolia. The roots were processed into chips by cleaning with de-ionized water, then with ultrafiltered water. Portions of contaminated surface were removed and the roots were cut into chips with a thickness of 2-5 mm. The chips were then sterilized and dried.

The chips were extracted first with 0.5 M $KH_2PO_4$ extraction at 100° C. for 3 h and then extracted with water at 100° C. for 3 h and repeated. The pooled extracts were centrifuged and ultrafiltered. The resulting solution was concentrated, precipitated first with 35% ethanol, then with 80% ethanol. The 80% ethanol precipitation was dissolved in water and spray-dried to obtain a crude extract.

The crude extract was run first through a SP cation exchange chromatography column, then a Q anion exchange chromatography column. The eluate was ultra filtered.

After concentration, the resulting eluate was hydrolyzed with hydrochloric acid (conc. 0.3M) for 3 hours, at 22° C. After neutralization, ultrafiltration and lyophilization of the high-yield extract is obtained in 3.3% yield based on crude extract.

Analysis of the High-Yield Extract

The glycosyl-residue composition was determined by GLC of TMS-methyglycoside derivatives. Ara, Gal, GalA, and Glc are the major sugar residues in the drug substance. The glycosyl-residue composition results are shown in Table 4 below.

TABLE 4

The glycosyl-linkage compositions in the high-yield extract.

| Glycosyl-residue | Mol % |
|---|---|
| Ara | 57.0 |
| Rha | 8.2 |
| Xyl | 2.7 |
| GalA | 13.8 |
| Gal | 13.1 |
| Glc | 4.7 |
| 4-0-Me-GlcA | 0.4 |

Note that the Ara:Gal ratio is 4.35. The protein content was determined using a BCA Protein Microassay. The protein content of the high-yield extract is shown in Table 5 below.

TABLE 5

The protein content in the high yield extract.

| Sample | Protein content (%) |
|---|---|
| AGP-P-05 | 0.67 |

The hydroxyproline content of the high-yield extract was determined by a colorimetric assay and is presented in Table 6 below.

TABLE 6

The hydroxyproline content of the high yield extract.

| Sample | Hyp (%) |
|---|---|
| AGP-P-05 | 0.34 |

EXAMPLE 3

Increasing Yield by Extracting with Milder Acid Conditions

This example shows that yield of the useful extract can be increased using milder acid conditions. An first extract is produced using conditions of 0.5M HCl, 6 hours of hydrolysis time, and 22° C.; and, the yield of the first extract is compared to the yield of a second extract and a third extract produced using milder acid conditions of 0.3M HCl, 3 hours hydrolysis time and 22° C. Table 7 shows a substantial increase in yield when using milder conditions.

TABLE 7

Yield Increase of extract obtained using milder conditions.

| | First Extract 0.5M HCl, 6 hrs, 22° C. | Second Extract 0.3M HCl, 3 hrs, 22° C. | Third Extract 0.5M HCl, 6 hrs, 22° C. |
|---|---|---|---|
| Ara:Gal | 2.9:1 | 4.3:1 | 4.0:1 |
| Protein content (BCA, %) | 1.01% | 0.67% | 0.64 |
| Endotoxin content (Endospecy, EU/mg) | 0.52 | 0.43 | 0.27 |

TABLE 7-continued

Yield Increase of extract obtained using milder conditions.

|  | First Extract 0.5M HCl, 6 hrs, 22° C. | Second Extract 0.3M HCl, 3 hrs, 22° C. | Third Extract 0.5M HCl, 6 hrs, 22° C. |
| --- | --- | --- | --- |
| hyP content | 0.42 | 0.34 | 0.35 |
| Yield (% of crude extract) | 2.4 | 3.3 (32% increase) | 3.1 (24% increase) |

EXAMPLE 4

Increasing Platelet Levels by Administering the Purified Extract to a Mammal that has Received Sublethal Irradiation This example shows that the purified extract stimulates platelet levels in a mammal that received a sublethal dose of x-rays. BALB/c mice were used in this experiment, and a portion of the mice received a sublethal dose of x-rays, 500 cGy, on day 0, causing a decrease in platelet level and thrombocytopenia. Platelet levels were measured in (a) normal mice, not subject to either irradiation or administration of the purified extract; (b) control mice receiving x-rays accompanied only by saline i.p.; (c) experimental mice receiving x-rays accompanied by 250 mg/kg of the purified extract in saline for 10 injections at a rate of 5 injections per week starting on day 0 of the irradiation and continuing through day 14 of the experiment; and (d) experimental mice receiving x-rays accompanied by 100 mg/kg/day of the purified extract starting on day 0 of the irradiation and continuing every day through day 25 of the experiment.

In the mice receiving 250 mg/kg of the purified extract in saline for 10 injections s.c. at a rate of 5 injections per week starting on day 0 of the irradiation and continuing through day 14 of the experiment, the sublethal x-rays caused a decrease in the platelet level that was first measured on day 10. When comparing the control group to the experimental mice receiving 100 mg/kg/day of the purified extract starting on day 0 of the irradiation and continuing through day 25 of the experiment, the purified extract showed an increase in platelet levels in the blood on day 14, and the difference between the low level of platelets found in the blood of EP011-treated mice compared to the control group increased after day 14 and remained evident through day 25. Accordingly, the purified extract increased the level of platelets in the blood of sublethally irradiated mice and enhanced the recovery of the platelet level from the radiation treatment.

EXAMPLE 5

Increasing Platelet Levels by Administering the High-Yield Extract, Alone and in Comparison to a Hematopoietic Agent Alone, to a Mammal that has Received Sublethal Irradiation This example shows that the high-yield extract stimulates platelet levels in a mammal that received a sublethal dose, 500 cGy, of x-rays. BALB/c mice were used in this experiment, and a portion of the mice received a sublethal dose of x-rays, 500 cGy, on day 0. Platelet levels were measured in (a) normal mice, not subject to either irradiation or administration of the high-yield extract; (b) control mice receiving x-rays accompanied only by saline i.p.; (c) experimental mice receiving x-rays accompanied by 250 mg/kg/day of the high-yield extract in saline; (d) experimental mice receiving x-rays accompanied by 100 mg/kg/day of the high yield extract; (e) experimental mice receiving x-rays accompanied by 50 mg/kg/day of the high yield extract; and (f) experimental mice receiving x-rays accompanied by G-CSF treatment. The high-yield extract was administered s.c. every day for days 0-4, and then 3 times/week for the next three weeks, administering the high-yield extract on days 7-9, 14-16, and 21-23.

FIG. 1 shows the response of the platelet level in BALB/c mice to the high-yield extract following administration of a sublethal dose of radiation, according to some embodiments. As can be seen from FIG. 1, the x-rays caused a decrease in the platelet level, causing a decrease in platelet level and thrombocytopenia at about 10 days post-irradiation. Treatment with the high-yield extract was given at 250 mg/kg in saline for 10 injections with 5 injections per week starting on day 0. The high-yield extract was effective at restoring 50% of normal platelet counts about 3-5 days earlier than the saline control group and, thus, the treatment increased the amount of platelets in the blood of sublethally irradiated mice and enhanced platelet recovery following radiation treatment. The effects of G-CSF (NEUPOGEN) was shown in FIG. 1 for purposes of comparison.

EXAMPLE 6

Increasing Platelet Levels by Administering the High-Yield Extract, Alone and in Combination with a Hematopoietic Agent, to a Mammal that has Received Chemotherapy This example shows that administration of the high-yield extract accelerates recovery from chemotherapy by stimulation of platelet levels and, thus, treating thrombocytopenia caused by the chemotherapy.

Platelet levels were measured in (a) normal mice, not subject to either chemotherapy or administration of the high-yield extract; (b) control mice receiving chemotherapy i.v. accompanied only by saline i.p.; (c) experimental mice receiving chemotherapy accompanied by 200 mg/kg/day s.c. of the high-yield extract in saline; (d) experimental mice receiving chemotherapy accompanied by 250 mg/kg/day s.c. of the high-yield extract in saline; (e) experimental mice receiving chemotherapy accompanied by 400 mg/kg/day s.c. of the high-yield extract in saline; (d) experimental mice receiving chemotherapy accompanied by 200 μg G-CSF in saline; and (e) experimental mice receiving chemotherapy accompanied by 250 mg/kg/day s.c. of the high-yield extract in saline, and by 200 μg G-CSF in saline.

The mice used were BALB/c mice, and were injected twice with 4 mg/kg mitomycin C (MMC) i.v., once on day "−1" and once on day 0. The mice also received 7 daily injections of 250 mg/kg/day s.c. of the high yield extract starting on day 0 through day 6.

Figure 2:
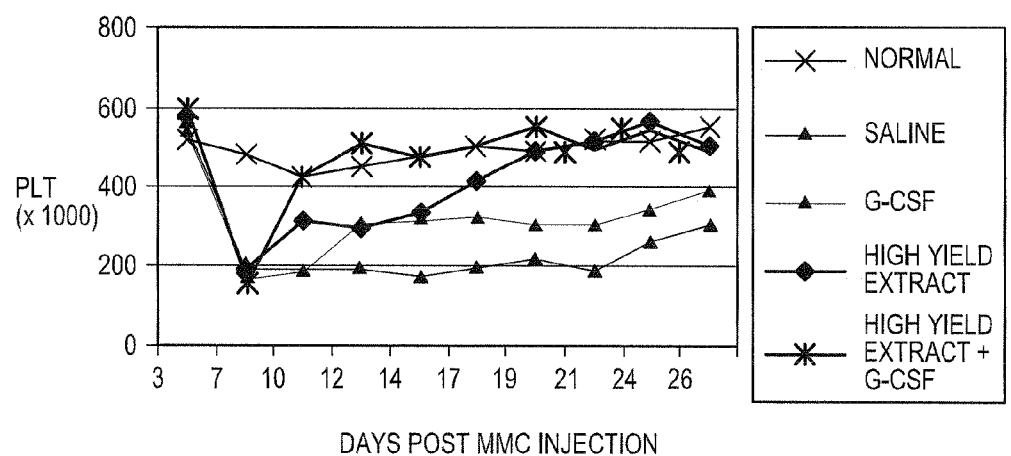
FIG. 2 shows that mitomycin induced thrombocytopenia 7 days after injection in BALB/c mice, according to some embodiments.

FIG. 2 shows that mitomycin induced thrombocytopenia 7 days after injection in BALB/c mice, according to some embodiments. The control mice treated with saline only recovered to 60% of a normal platelet count, or about 300× $10^3/\mu L$, by the end of the experiment at day 26, whereas experimental mice treated with the high-yield extract reached 60% of a normal platelet count by around day 10 and 100% of a normal platelet count by around day 19, where a normal platelet count was about 500×$10^3/\mu L$. Accordingly, the high-yield extract induced platelet recovery in chemotherapy-induced thrombocytopenia.

The high-yield extract accelerates recovery of platelets or megakaryocytes after exposure to chemotherapy. Although FIG. 2 highlights similar results using the chemotherapy and extract amounts described above, data not shown illustrated that MMC treatment generally caused platelet counts to decrease on day 3 and reach a nadir of 25% of the basal platelet count level by around day 10. Control mice treated with saline only recovered to about 50% of the basal platelet count level by day 24, whereas experimental mice treated with 200-400 mg/kg/day of the high-yield extract increased recovered to about 40-50% of the basal platelet count level by day 10 and continued to recover platelet count thereafter. In mice treated with 400 mg/kg/day of the high-yield extract, the platelet counts reached 100% of the basal platelet count level by day 21, whereas the control mice that received only saline were still at about 50% of the basal platelet count level. The high-yield extract reduced the duration of the thrombocytopenia from 6 days in the control mice that received only saline to 0 days in the experimental mice receiving the high-yield extract.

In FIG. 2, the mice receiving the G-CSF (NEUPOGEN) received either 7 injections of 200 µg NEUPOGEN in saline starting on day 0, or 7 injections of 250 mg/kg s.c. of the high-yield extract 200 µg and NEUPOGEN in saline starting on day 0. The results show that the combination of the high-yield extract with NEUPOGEN accelerated recovery of platelets when compared to mice receiving either treatment alone, and the combination therapy obtained the normal, control platelet levels rapidly, by day 10. A particularly interesting finding was that the high-yield extract and the combination therapy both outperformed G-CSF administration alone, which failed to reach normal platelet levels by the end of the experiment, after day 26. The combination of G-CSF with the high-yield extract, however, obtained normal platelet counts about 9 days earlier than through the administration of the high-yield extract alone.

Accordingly, administration of the high-yield extract to mammals having chemotherapy-induced thrombocytopenia at least (1) eliminates severe thrombocytopenia, defined as a platelet count of $<200 \times 10^{-9}/L$; (2) reduces the severity of the platelet nadir of a thrombocytopenic condition, in general; (3) shortens the duration of a thrombocytopenic condition; (4) accelerates platelet recovery, in a dose-dependent manner; and (5) provides a significantly enhanced platelet recovery through the co-administration of G-CSF.

EXAMPLE 7

Stimulating Production of White Blood Cells by Administering the High-Yield Extract to a Mammal that has Received Sublethal Irradiation This example shows that the high-yield extract can be used to stimulate the recovery of white blood cells in a mammal exposed to radiation that has suppressed bone marrow function or hematopoiesis. As such, the extract can assist where a reduced level of white blood cells otherwise can leave the mammal vulnerable to infections.

This example shows that the high-yield extract stimulates recovery of white blood cells in a mammal that received a sublethal dose of x-rays. BALB/c mice were used in this experiment, and a portion of the mice received a sublethal dose of x-rays, 500 cGy, on day 0. Cell counts were measured in (a) normal mice, not subject to either irradiation or administration of the high-yield extract; (b) control mice receiving x-rays accompanied only by saline i.p.; (c) experimental mice receiving x-rays accompanied by 250 mg/kg of the purified extract in saline for 10 injections at a rate of 5 injections per week starting on day 0 of the irradiation and continuing through day 14 of the experiment; and (d) experimental mice receiving x-rays accompanied by 200 µg of G-CSF in saline starting on day 0 of the irradiation and continuing through day 26 of the experiment.

Figure 3:
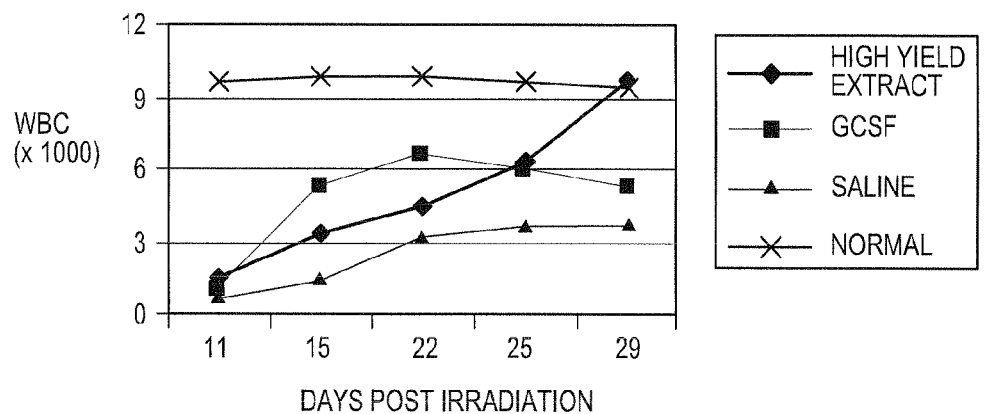
FIG. 3 shows the recovery of white blood cells in irradiated BALB/c mice after administration of the high-yield extract, according to some embodiments.

FIG. 3 shows the recovery of white blood cells in irradiated BALB/c mice after administration of the high-yield extract, according to some embodiments. Severe leukopenia was seen at 7-10 days after irradiation, where the mice showed a white blood cell count of about 600-1000/µl. The high-yield extract induced recovery of white blood cells in about 21-25 days, and the white blood cell count in control mice treated with saline only did not recover by the end of the experiment. A differential count indicated that the high-yield extract also induced recovery of lymphocytes.

Accordingly, comparing FIG. 3 to FIG. 2, it can be seen that the high-yield extract accelerates recovery of white blood cells, shortens the duration of leukopenia, as well as increases platelet count in a BALB/c mouse subjected to a sublethal dose of x-rays.

EXAMPLE 8

Enhancing Platelet Recovery in a Mammal Suffering from Radiation-Induced Thrombocytopenia by Co-Administering the High-Yield Extract with an Agent that Stimulates Hematopoiesis This example shows that the co-administration of the high-yield extract with G-CSF can stimulate platelet production in a BALB/c mouse that was sublethally irradiated.

BALB/c mice were used in this experiment. A portion of the mice received a sublethal dose of x-rays, 500 cGy, on day 0. Platelet levels were measured in (a) normal mice, not subject to either irradiation or administration of the high-yield extract; (b) control mice receiving x-rays accompanied only by saline i.p.; (c) experimental mice receiving x-rays accompanied by 250 mg/kg/day of the high-yield extract in saline s.c. for 7 daily injections starting on day 0 of the irradiation; (d) experimental mice receiving x-rays accompanied by a co-injection of 250 mg/kg/day of the high yield extract and 1 µg/kg G-CSF in saline s.c. for 7 daily injections starting on day 0 of the irradiation; (f) experimental mice receiving x-rays accompanied by a co-injection of 250 mg/kg/day of the high yield extract and 100 µg/kg G-CSF in saline s.c. for 7 daily injections starting on day 0 of the irradiation.

Figure 4:
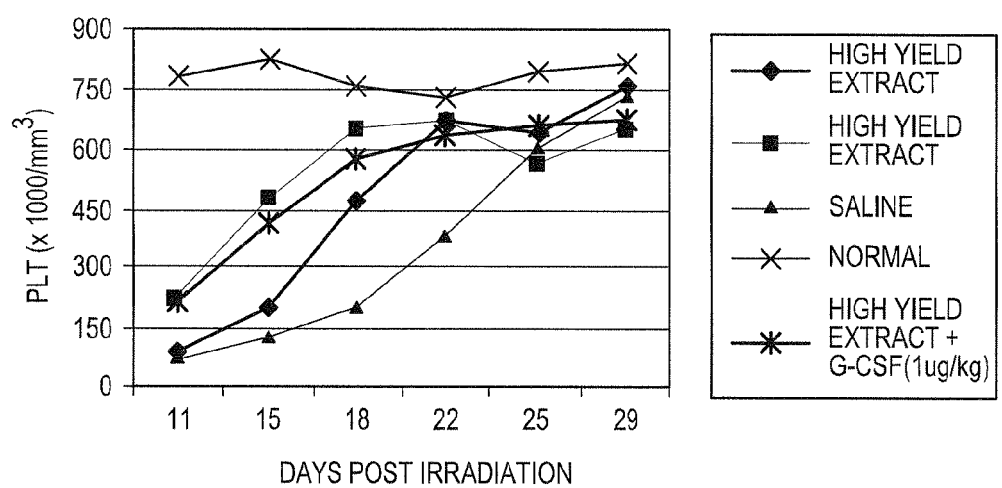
FIG. 4 shows rate of recovery of platelet count in an irradiated BALB/c mouse when the high-yield extract and G-CSF are co-injected, according to some embodiments.

FIG. 4 shows rate of recovery of platelet count in an irradiated BALB/c mouse when the high-yield extract and G-CSF are co-injected, according to some embodiments. The rate of recovery was nearly the same when mice were co-injected with the high-yield extract and either 1 µg/kg G-CSF or 100 µg/kg G-CSF. In both groups, mice recovered to about 50% of the normal platelet count by day 15, whereas mice receiving only the high-yield extract recovered to about 50% of the normal platelet count by day 18. In contrast, it took the control mice until about day 22 to reach about 50% of the normal platelet count.

EXAMPLE 9

Enhancing White Blood Cell Recovery in a Mammal Irradiated by a Sublethal Dose of X-Rays by Co-Administering the High-Yield Extract with an Agent that Stimulates Hematopoiesis This example shows that the co-administration of the high-yield extract with G-CSF can stimulate white blood cell production in a BALB/c mouse that was sublethally irradiated.

BALB/c mice were used in this experiment. A portion of the mice received a sublethal dose of x-rays, 500 cGy, on day 0. Platelet levels were measured in (a) normal mice, not subject to either irradiation or administration of the high-yield extract; (b) control mice receiving x-rays accompanied only by saline i.p.; (c) experimental mice receiving x-rays accompanied by 250 mg/kg/day of the high-yield extract in saline s.c. for 10 injections at a rate of 5 injections per week starting on day 0 of the irradiation and continuing through day 14 of the experiment; (d) experimental mice receiving x-rays accompanied by a co-injection of 250 mg/kg/day of the high yield extract and 100 μg/kg G-CSF in saline s.c. for 10 injections at a rate of 5 injections per week starting on day 0 of the irradiation and continuing through day 14 of the experiment; and (e) experimental mice receiving x-rays accompanied by a co-injection of 250 mg/kg/day of the high yield extract and 1 μg/kg G-CSF in saline s.c. for 10 injections at a rate of 5 injections per week starting on day 0 of the irradiation and continuing through day 14 of the experiment.

Figure 5:
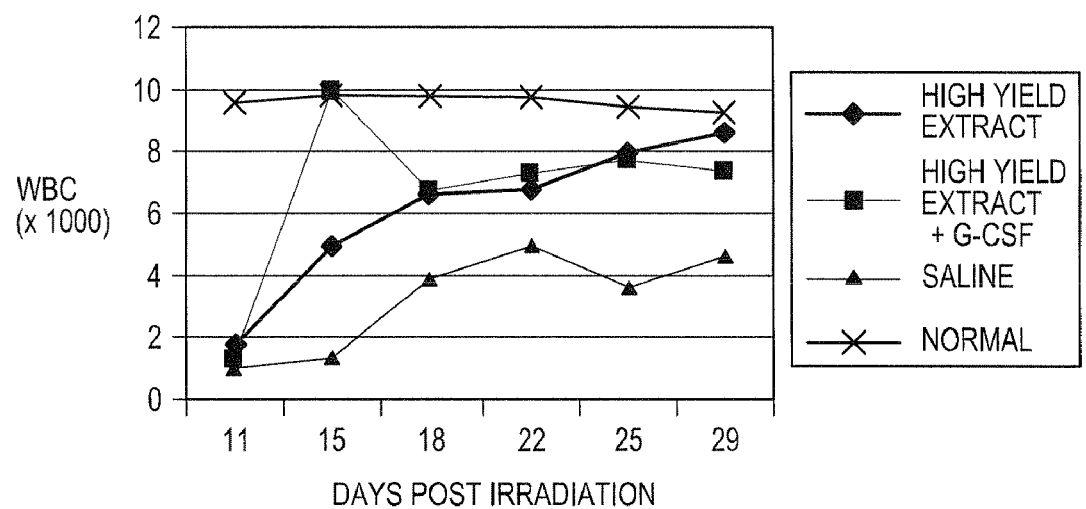
FIG. 5 shows the rate of recovery of white blood cell count in an irradiated BALB/c mouse when the high-yield extract and G-CSF are co-injected, according to some embodiments.

FIG. 5 shows the rate of recovery of white blood cell count in an irradiated BALB/c mouse when the high-yield extract and G-CSF are co-injected, according to some embodiments. The radiation created a marked reduction in white blood cells. The injection of the high-yield extract alone induced a slow rate of white blood cell recovery. And, although not shown in FIG. 5, the rate of recovery was nearly the same again when mice were co-injected with the high-yield extract and either 1 μg/kg G-CSF or 100 μg/kg G-CSF. The co-injection resulted in a transient spike to a normal white blood cell count on day 15, whereas the high-yield extract alone induced recovery to 50% of the normal count. From day 18 until the end of the experiment there was little difference between the co-injection and the administration of the high-yield extract alone. Both treatments showed 60% of the normal count and fully recovered the normal count by day 29. The control mice receiving only saline shoed 40% of the normal white blood cell count at day 29.

EXAMPLE 10

Treating ITP Patients in Taiwan

A purified extract taught herein was used to treat humans in an ongoing, open-label, multi-center and dose-finding trial with two parallel study groups. The safety and efficacy of a treatment using the extract was evaluated in subjects having chronic idiopathic thrombocytopenia. The trial was conducted at two leading medical centers in Taiwan.

Figure 6:
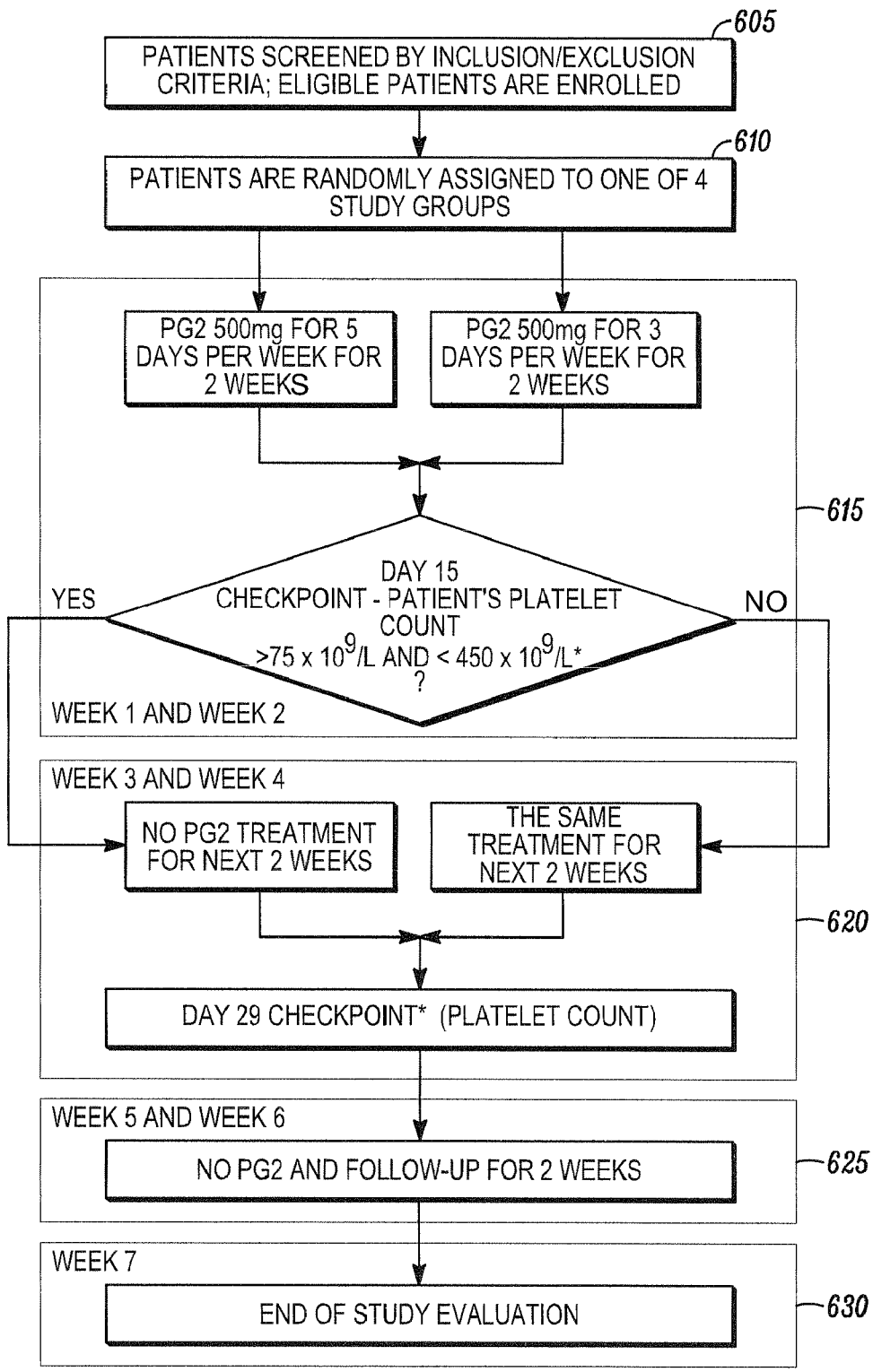
FIG. 6 illustrates a flowchart of the clinical trial in Taiwan, in which the patients were diagnosed as having chronic idiopathic thrombocytopenia according to The American Society of Hematology (ASH) guidelines.

FIG. 6 illustrates a flowchart of the clinical trial in Taiwan, in which the patients were diagnosed as having chronic idiopathic thrombocytopenia according to The American Society of Hematology (ASH) guidelines. The ASH guidelines include, as shown in FIG. 6, screening 605 for at least six months using inclusion and exclusion criteria. And, during a study period of six weeks, all patients were allowed to take corticosteroid or other therapies as established prior to the study. The study further included randomly assigning 610 the patients into one of four study groups.

The study further included administering 615 the purified extract by one of two regimens during the first two weeks: (Regimen 1) 500 mg of the extract by IV infusion for about 3 hours (2.5 to 3.5 hours) for 5 constitutive days per week; or, (Regimen 2) 500 mg of the extract by IV infusion for about 3 hours (2.5 to 3.5 hours) for 3 days per week. The next step included evaluating 620 the response: (1) if the patient's platelet count improved to or above $75 \times 10^9/L$ by day 15 but under $450 \times 10^9/L$, the treatment including discontinuing 620 the administration of the extract for the next two weeks; and (2) if the patient's platelet count did not improve to or above $75 \times 10^9/L$ by day 15 but under $450 \times 10^9/L$, the treatment included continuing administration of the extract continued for two more weeks.

During the fifth and sixth weeks of the study, the patients were followed up while denying 625 administration of the extract. At any time during the study, if the platelet count elevated to $450 \times 10^9/L$ or more, the patient stopped receiving any more extract and was monitored until ending 630 the study. Rescue therapy, in the case of severe bleeding, was designed to include IVIG, steroids or platelet transfusion, was used and recorded. The other treatments deemed necessary for non-ITP-related medical conditions were permitted.

Based on the results of the study, the extract appears safe and effective in increasing the platelet count among ITP patients.

EXAMPLE 11

Treating ITP Patients in China

The purified extract was used in a chronic and refractory ITP case study in China. The Patient had been diagnosed as ITP for several years, and there was no effective treatment including a splenectomy. The patient was treated with prednisolone or triamcinolone for a period of a few years to maintain the platelet count, and several bleeding events were recorded. At the end of that treatment period, the patient was treated with triamcinolone combined with the extract (250 mg/day) daily for 2 weeks. After a 2-week treatment, as shown in Table 8, the patient's platelet count was recovered from $44 \times 10^9/L$ to $110 \times 10^9/L$.

TABLE 8

| | Year | | | |
|---|---|---|---|---|
| | Year 1 | Year 2 | Year 3 | Year 4 |
| | Treatment | | | |
| | Prednisolone 2.5 mg | Prednisolone 1.25 mg | Prednisolone 5 mg | Triamcinolone 4 mg |
| Platelet Count | $29 \times 10^9/L$ | $24 \times 10^9/L$ | $26 \times 10^9/L$ | $44 \times 10^9/L$ |

| | Year February, Year 5 | |
|---|---|---|
| | 1st week | 2nd week |
| | Treatment | |
| | Triamcinolone 4 mg + PG2 | Triamcinolone 4 mg + PG2 |
| Platelet Count | $79 \times 10^9/L$ | $110 \times 10^9/L$ |
| Platelet Count | $71 \times 10^9/L$ | $81 \times 10^9/L$ |

| | Year March, Year 5 | | |
|---|---|---|---|
| | Before PG2 treatment | 1st week | 2nd week |
| | | Treatment | |
| | Prednisolone 5 mg + PG2 | Prednisolone 5 mg + PG2 | Prednisolone 5 mg + PG2 |
| Platelet Count | $108 \times 10^9/L$ | $118 \times 10^9/L$ | Data not shown |

This result provided a recovery far beyond the use of conventional therapy of steroids, and also showed a sustained effect of three months beyond the dosing of the extract. When the platelet count approached normal, an additional dosing of the extract was given for two more weeks. During the next three months, there was no overshooting of the platelet counts, which is significant, since the extract seems to exert a self-feedback mechanism as a control to overshooting of platelet count.

EXAMPLE 11

Treating ITP Patients—Individual Studies

The objective this study was to evaluate the efficacy and safety of the purified extract in individual patients having chronic idiopathic thrombocytopenia (ITP), which included patients having the condition for 6 months or longer with a maintenance ITP treatment. The study was open-labeled, randomized, with a two-study cohort. The primary endpoint was platelet count response.

A female patient (R01001) was diagnosed as having ITP for more than 10 years and had been treated using prednisolone (10 mg QD). The patient received the purified extract for 5 days/week for 4 weeks, and the results are shown in Table 9.

TABLE 9

| Date | Study Schedule | Platelet Count ($10^3$/ul) |
|---|---|---|
| 2008 Nov. 24 | screening | 8,000 |
| 2008 Dec. 01 | Day 1 | 10,000 (baseline) |
| 2008 Dec. 08 | Day 8 | 8,000 |
| 2008 Dec. 15 | Day 15 | 12,000 |
| 2008 Dec. 22 | Day 22 | 8,000 |
| 2008 Dec. 29 | Day 29 | 12,000 |
| 2009 Jan. 12 | Day 43 | 23,000 |

It should be appreciated that the platelet count was double the baseline and recovered to 23,000 after treatment with the purified extract as a responder to the treatment. No adverse events occurred.

A female patient (R02001), 46 years of age, was diagnosed as having ITP for more than 5 years and had been treated using prednisolone (20 mg QD). The patient received the purified extract for 5 days/week for 3 weeks, and the results are shown in Table 10.

TABLE 10

| Date | Study Schedule | Platelet Count ($10^3$/ul) |
|---|---|---|
| 2008 Dec. 30 | Day 1 | 3,000 (baseline) |
| 2009 Jan. 05 | Day 8 | 7,000 |
| 2009 Jan. 12 | Day 15 | 4,000 |
| 2009 Jan. 19 | Day 22 | 5,000 |
| 2009 Feb. 02 | Day 29 | 11,000 |
| 2009 Feb. 17 | Day 43 | 6,000 |

It should be appreciated that the platelet count recovered to 11,000 after treatment with the purified extract. No adverse events occurred.

A male patient (R01002), 61 years of age, was diagnosed as having ITP for more than 10 years and had been treated using prednisolone (10 mg QD). The patient received the purified extract for 3 days/week for 2 weeks, and the results are shown in Table 11.

TABLE 11

| Date | Study Schedule | Platelet Count ($10^3$/ul) |
|---|---|---|
| 2009 May 18 | Day 1 | 37,000 (baseline) |
| 2009 May 25 | Day 8 | 11,000 |
| 2009 Jun. 01 | Day 15 | 84,000 |
| 2009 Jun. 03 | Day 17 | 58,000 |
| 2009 Jun. 08 | Day 22 | 55,000 |
| 2009 Jun. 15 | Day 29 | 31,000 |
| 2009 Jun. 29 | Day 43 | 14,000 |

It should be appreciated that the platelet count recovered from 37,000 to 84,000 after treatment with the purified extract as a responder to the treatment. No adverse events occurred.

Finally, a female patient (R02002), 60 years of age, was diagnosed as having ITP about 4 years ago and had been treated using prednisolone (15 mg QD). The patient received the purified extract for 3 days/week for 3 weeks (treatment ongoing), and the results are shown in Table 12.

TABLE 12

| Date | Study Schedule | |
|---|---|---|
| | | Platelet Count ($10^3$/ul) |
| 2009 Jul. 06 | Day 1 | 8,000 (baseline) |
| 2009 Jul. 13 | Day 8 | 6,000 |
| 2009 Jul. 20 | Day 15 | 54,000 |
| | | Adverse Events |
| 2009 Jul. 06 | Day 1 | Allergic reaction |
| 2009 Jul. 08 | Day 3 | Skin rash |

It should be appreciated that the platelet count recovered from 8,000 to 54,000 after treatment with the purified extract as a responder to the treatment.

We claim:
1. A composition comprising a purified extract of the roots of *Astragalus membranaceus*, wherein the extract comprises:
   an arabinose:galactose ratio greater than 4.0:1 to 5.0:1;
   from about 5% to about 10% rhamnose;
   from about 15% to about 20% galactose;
   from about 10% to about 20% galacturonic acid;
   not more than 2% by weight protein, and,
   from about 10% to about 15% glucose;
   wherein,
   the extract is prepared using a first process that includes isolating a crude extract from *Astragalus membranaceus* and mildly treating the crude extract with an acid, the mildly treating including applying the acid to the crude extract at a concentration ranging from about 0.05M to about 0.5M, at a temperature ranging from about 15° C. to 25° C., and for a time ranging from about 1 hour to about 24 hours, wherein the temperature and time for applying the acid are selected to obtain the arabinose:galactose ratio, the galactose content, the glucose content, and a high yield; and,
   the extract is substantially higher in yield than an extract of the *Astragalus membranaceus* produced using a second process that includes applying the acid to the crude extract at a temperature and time selected to obtain an arabinose:galactose ratio of less than 3.5:1, 20%-35% galactose, and less than about 10% glucose.
2. The composition of claim 1, wherein the *Astragalus membranaceus* is *A. membranaceus* Bge, var, *mongholicus* (Bge.) Hsiao or *A. membranaceus* (Fisch.) Bge.

3. The composition of claim 1, wherein the *Astragalus membranaceus* was grown in Inner Mongolia or Shanxi province, Peoples' Republic of China.

4. The composition of claim 1, wherein the roots are from *Astragalus membranaceus* plants that are about two years of age.

5. The composition of claim 1 having a weight-average molecular weight of at least 100 kiloDaltons.

6. The composition of claim 1 having at least 80% by weight.

7. The composition of claim 1, wherein the acid is trichloroacetic acid or hydrochloric acid.

8. The composition of claim 1 having a pH in aqueous solution ranging from about 4.5 to about 6.5.

9. The composition of claim 1, further comprising an agent that stimulates hematopoiesis.

10. The composition of claim 1, further comprising an agent selected from the group consisting of granulocyte colony stimulating factor, granulocyte macrophage colony stimulating factor, erythropoietin and erythropoiesis stimulating protein, thrombopoietin, and interleukin-3.

11. An aqueous injectable formulation comprising a therapeutically effective amount of the composition of claim 1 and an aqueous injectable excipient.

12. A method of preparing the extract of claim 1 comprising:
   isolating a crude extract from *Astragalus membranaceus* and mildly treating the crude extract with an acid; and,
   mildly treating including applying the acid to the crude extract at a concentration ranging from about 0.05M to about 0.5M, at a temperature ranging from about 15° C. to 25° C., and for a time ranging from about 1 hour to about 24 hours, wherein the temperature and time for applying the acid are selected to obtain an arabinose: galactose ratio greater than 4.0:1 to 5.0:1; from about 5% to about 10% rhamnose; from about 15% to about 20% galactose; from about 10% to about 20% galacturonic acid; from about 10% to about 15% glucose and having not more than 2% by weight protein.

\* \* \* \* \*